(12) United States Patent
Vatner et al.

(10) Patent No.: US 7,160,859 B2
(45) Date of Patent: Jan. 9, 2007

(54) MST1 MODULATION OF APOPTOSIS IN CARDIAC TISSUE AND MODULATORS OF MST1 FOR TREATMENT AND PREVENTION OF CARDIAC DISEASE

(75) Inventors: Stephen F. Vatner, New York, NY (US); Junichi Sadoshima, Berkeley Heights, NJ (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 10/683,576

(22) Filed: Oct. 10, 2003

(65) Prior Publication Data

US 2004/0213794 A1  Oct. 28, 2004

Related U.S. Application Data

(60) Provisional application No. 60/418,002, filed on Oct. 11, 2002.

(51) Int. Cl.
*A61K 38/00* (2006.01)
*C07K 1/00* (2006.01)
*G01N 33/53* (2006.01)

(52) U.S. Cl. .................... 514/12; 530/350; 435/7.1
(58) Field of Classification Search ............ 514/114, 514/44, 354, 403, 510; 424/93.3; 435/320, 435/325
See application file for complete search history.

(56) References Cited

U.S. PATENT DOCUMENTS

| 4,975,444 | A  | * | 12/1990 | Danilewicz et al. | 514/354 |
| 6,225,288 | B1 | * | 5/2001 | Han et al. | 514/19 |
| 2003/0130216 | A1 | * | 7/2003 | Laugwitz et al. | 514/444 |
| 2004/0009957 | A1 | * | 1/2004 | Kukreja | 514/114 |

OTHER PUBLICATIONS

Yamamoto et al, Chelerythrine rapidly induces apoptosis through generation of reactive oxygen species in cardiac myocytes, J Mol Cell Cardiol. Oct. 2001;33(10):1829-48.*

* cited by examiner

*Primary Examiner*—Jon Weber
*Assistant Examiner*—Robert B. Mondesi
(74) *Attorney, Agent, or Firm*—Klauber & Jackson, LLC.

(57) ABSTRACT

The present invention relates to methods and agents for treatment, amelioration and prevention of cardiac disease, including cardiac myopathy, chronic heart failure and for management and reduction of cardiac myocyte death which may occur in response to ischemia/reperfusion or following myocardial infarction or other injury to the heart. The invention relates to methods for screening cardiotherapeutic compounds, including compounds which modulate cardiac myocyte apoptosis, particularly targeting Mst1 and the Mst1 pathway. The present invention further encompasses compounds identified by such screening methods and compositions comprising these compounds. The invention also provides methods for treatment, amelioration and prevention of cardiac disease comprising administering compounds or agents which modulate, particularly inhibit, Mst1 or the Mst1 kinase pathway, including administering a nucleic acid encoding an altered form of Mst1, particularly a dominant negative Mst1, which acts as an antagonist of Mst1.

17 Claims, 31 Drawing Sheets

COX VIIa

COX IV

COX Vb

N = nontransgenic, T = transgenic

Doxo 0.5μM

Doxo 0.1μM

Control Myocytes

MST1 MODULATION OF APOPTOSIS IN CARDIAC TISSUE AND MODULATORS OF MST1 FOR TREATMENT AND PREVENTION OF CARDIAC DISEASE

RELATED APPLICATIONS

The present application claims the benefit of the filing date pursuant to 35 U.S.C. § 119 of provisional application Ser. No. 60/418,002, filed Oct. 11, 2002, which is incorporated herein by reference in its entirety.

GOVERNMENTAL SUPPORT

The research leading to the present invention was supported, at least in part, by a grant from the National Institutes of Health, Grant Numbers HL-59139,HL-33107, HL-33065, HL65182, HL-65183, AG-14121, HL-69020, HL-67724 and HL-67727. Accordingly, the Government may have certain rights in the invention.

FIELD OF THE INVENTION

The present invention relates to methods and agents for treatment, amelioration and prevention of cardiac disease, including cardiac myopathy, chronic heart failure and for management and reduction of cardiac myocyte death which may occur in response to ischemia/reperfusion or following myocardial infarction or other injury to the heart. The invention relates to methods for screening cardiotherapeutic compounds, including compounds which modulate cardiac myocyte apoptosis, particularly targeting Mst1 and the Mst1 pathway. The present invention further encompasses compounds identified by such screening methods and compositions comprising these compounds.

BACKGROUND OF THE INVENTION

Intensive studies in the past decade have shown that cardiac myocyte death, which has characteristics of apoptosis, occurs in response to ischemia/reperfusion (I/R) and during cardiac remodeling after myocardial infarction (1–9). Although controversies still exist regarding the occurrence of apoptosis vs oncosis in the ischemic heart (10,11), it seems established that the signaling mechanisms promoting myocyte cell death, including caspases, are activated by I/R and in cardiomyopathy (12–16) (reviewed in 47). Recent evidence suggests that myocyte proliferation could take place in response to the loss of cardiac myocyte after myocardial infarction (17). However, considering the limited capacity of terminally differentiated cardiac myocytes for proliferation, it is important to understand how these cell death promoting signaling mechanisms are activated by I/R and in myopathic hearts in order to establish interventions efficiently preventing the cell loss in various stages of heart diseases (10). It has been shown that intracellular stress-responsive protein kinases, including JNKs and p38-MAPKs, are activated by I/R in the heart (18–23). Although these kinases are likely to affect both cell death and cell survival, the roles of the stress-responsive protein kinases (SRPKs) in cardiac myocyte apoptosis are not fully understood. Furthermore, the SRPK selectively promoting cardiac myocyte apoptosis has not been identified in vivo.

Mst1 (mammalian sterile 20-like kinase-1) is a ubiquitously expressed serine/threonine kinase (24,25), which belongs to a mammalian sterile 20 (STE 20)-like kinase family consisting of Pak1, Mst 1, Mst2, Khs, Gck, Sok1, Nik, Hpk1 and Sps1 (26,27). Increasing lines of evidence suggest that Mst1 and other STE20-like family kinases play an important role in mediating apoptosis (reviewed in (27)). Mst 1 is activated by some pro-apoptotic stimuli in fibroblastic and lymphocytic cell lines. However, stimuli shown to activate Mst1 are generally limited to non-physiological stresses, including genotoxic compounds and extreme heat shock (25,28–31). Mst1 can be an efficient mediator of apoptosis because it is cleaved by caspases and this cleavage increases kinase activities of Mst1, which in turn activates caspase 3 (32), thereby constituting a powerful amplification loop of apoptotic response (33). Importantly, however, whether or not activation of Mst1 is required for in vivo cell death in response to clinically relevant pathologic insults has not been determined in any organs, including the heart.

Despite a growing understanding that apoptosis plays a physiological role and potentially pathological role in the heart there still exists a significant need in the art for methods and agents for treatment, amelioration and prevention of cardiac disease, including cardiac myopathy, chronic heart failure and for management and reduction of cardiac myocyte death which may occur in response to ischemia/reperfusion or following myocardial infarction or other injury to the heart.

The citation of references herein shall not be construed as an admission that such is prior art to the present invention.

SUMMARY OF THE INVENTION

In accordance with the present invention, it has been recognized and demonstrated that stimulation or enhanced expression of Mst1 causes cardiac myocyte apoptosis and dilated cardiomyopathy, without any compensatory cardiac myocyte hypertrophy. In addition, specific inhibition of endogenous Mst1, for instance by dominant negative Mst1, inhibits cardiac myocyte apoptosis and myocardial infarction in response to ischemia/reperfusion (I/R). Inhibition of endogenous Mst1 also inhibits the negative cardiac effects of cardiotoxic drugs, including doxorubicin. In addition, on inhibition of endogenous Mst1, the cardiac dilation and cardiac dysfunction following myocardial infarction are significantly reduced. Thus, Mst1 plays an essential role in mediating apoptosis by clinically relevant pathologic stimuli in the heart and represents an important therapeutic target in ischemic heart diseases.

The invention relates to the application and use of modulators, including inhibitors, of Mst1 to treat or prevent heart disease. The invention relates to the use of modulators, particularly inhibitors, of the Mst1 kinase for amelioration, treatment or prevention of cardiac disease, particularly wherein it is desired to reduce or control cardiac myocyte apoptosis, including in congestive heart failure, cardiomyopathy, including ischemic and nonischemic cardiomyopathy, coronary artery disease, arrhythmias, fibrosis of the heart, valve defects, and atherosclerosis, as well as in instances where facilitation of enhanced heart function or maintenance of cardiac myocytes is desired.

In a particular aspect, the invention provides methods of modulating the apoptosis of cardiac myocytes and cardiac myopathy in a mammal by administration of a compound or agent that blocks or otherwise inhibits Mst1 or the Mst1 pathway. In one aspect, a method for modulating the apoptosis of cardiac myocytes and cardiac myopathy is provided whereby an effective amount of an inhibitor of Mst1 is administered.

In a further aspect, the invention provides a method for treating cardiac disease in a mammal comprising administering to said mammal an effective amount of an Mst1 inhibitor. In a particular aspect, the invention further provides a method for treating a cardiac disease or dysfunction selected from the group of congestive heart failure, cardiomyopathy, including ischemic and nonischemic cardiomyopathy, coronary artery disease, arrhythmias, fibrosis of the heart, valve defects, and atherosclerosis in a mammal comprising administering to said mammal an effective amount of an Mst1 inhibitor. In a still further aspect a method is provided for reducing the risk of cardiomyopathy or dysfunction in a mammal after said mammal has suffered a myocardial infarct or other coronary event wherein blood flow to the heart is compromised or significantly reduced comprising administering to said mammal an effective amount of an Mst1 inhibitor or Mst1 pathway inhibitor.

In a further aspect, the invention provides a method of cardioprotection, wherein an inhibitor of Mst1 is administered in conjunction with or following therapy with a compound or drug which is cardiotoxic or has potential to be cardiotoxic. In this method, an Mst1 modulator blocks or otherwise reduces the cardiotoxic effects of a drug or compound. In a particular embodiment, the drug or compound is a chemotherapeutic agent, particularly an anti-cancer agent, including but not limited to doxorubicin. In a further aspect, administration of the Mst1 modulator enables chemotherapeutic, particularly anti-cancer or anti-tumor compounds, treatment without significant cardiotoxic effects or permits prolonged chemotherapy or administration of higher concentrations or amounts of a potentially cardiotoxic drug.

In a further aspect, the invention provides a method for treating cardiac disease in a mammal comprising administering to said mammal an effective amount of an Mst1 inhibitor in combination with one or more other compounds for the treatment of heart disease, including but not limited to congestive heart failure, cardiomyopathy, including ischemic and nonischemic cardiomyopathy, coronary artery disease, arrhythmias, fibrosis of the heart, valve defects, and atherosclerosis. In particular, an effective amount of an Mst1 inhibitor may be used in combination with one or more compound for treatment of cardiac disease or of atherosclerosis, including but not limited to a beta-blocker, nitrate, calcium channel antagonists, angiotensin-converting enzyme (ACE) inhibitors, an anti-platelet drug, diuretics, digoxin and antilipemic agents, agents which alter cholesterol or lipid metabolism. Further examples of such or treatmantilipemic agents include, but are not limited to the statins, such as Lovastatin (Mevacor®), Atorvastatin (Lipitor®), Simvastatin (Zocor®), Cerivastatin (Baycol®), Pravastatin (Pravacol®), Fluvastatin (Lescol®) and Rosuvastatin; as well as other classes of compounds including cholesterol ester transfer protein inhibitors; cholesterol adsorption inhibitors (e.g., Ezetimide®); fibrates (e.g., Gemfibrozil®); nicotinic acid (e.g., niacin and analogs, Niaspan®); bile acid reuptake inhibitors; and modulators of nuclear hormone receptors such as PPARa, PPARb, PPARg, LXRa, LXRb, FXR, RORa and SHP.

The object of the invention extends to the provision of methods for screening for cardiotherapeutic compounds, particularly compounds which modulate cardiac myocytes, particularly apoptosis of cardiac myocytes, by using Mst1 or a member of the Mst1 pathway. In a particular object, methods are provided for screening compounds which modulate cardiac myocytes, by modulating Mst1, Mst1 kinase activity, or the Mst1 pathway, for instance by modulating caspase which activates Mst1 by caspase-mediated cleavage of the C-terminal inhibitory domain. In addition, the present invention encompasses compounds that are identified by the screening methods disclosed herein. Further provided are methods and compositions for modulating cardiac myocytes and thereby modulating cardiac disease and cardiac function.

A method of the invention involves screening cardiotherapeutic compounds and includes the steps of selecting compounds that modulate Mst1 or some portion of the Mst1 pathway, and performing assays with said compounds. The method of screening of the present invention may also include the step of identifying compounds that lead to reduction of cardiac myocyte apoptosis, or alternatively, to a decrease in levels or activity of Mst1. Selecting compounds that modulate Mst1 or the Mst1 pathway may involve different assays, such as, e.g., phosphorylation assays wherein a compound's ability to block phosphorylation of or by Mst1 or enhance dephosphorylation of Mst1 or a Mst1 target is determined directly or wherein the activity of a molecule downstream of Mst1 is determined. For instance, the phosphorylation of the Mst1 target myelin basic protein (MBP) can be assayed, including by incubation with labeled phosphate (e.g. $\gamma P^{32}$) and determining whether MBP is labeled. Compounds for screening may be selected from various libraries of small molecular weight compounds, peptides, or alternatively may be selected by homology modeling, computational modeling, and screening phage display libraries.

The invention thus includes an assay system for screening of potential drugs effective to modulate Mst1 activity of cardiac cells by interrupting or potentiating Mst1 or the Mst1 pathway. In one instance, the test drug could be administered to a cellular sample to determine its effect upon the kinase activity or phosphorylation status of Mst1 or an Mst1 target, by comparison with a control.

The present invention also includes compositions for treating or ameliorating cardiac disease, particularly for modulating apoptosis of cardiac myocytes. These compositions may comprise compounds identified by the screening methods disclosed herein. Thus, these compositions may be used to cardiac diseases or conditions where cardiac function or efficiency is compromised.

It is a thus an object of the present invention to provide pharmaceutical compositions for use in therapeutic methods for modulation of cardiac disease which comprise an Mst1 inhibitor. In a further aspect, the invention provides pharmaceutical compositions for use in therapeutic methods for modulation of cardiac disease which comprise an Mst1 inhibitor and one or more compounds for the treatment of heart disease, including but not limited to congestive heart failure, cardiomyopathy, including ischemic and nonischemic cardiomyopathy, coronary artery disease, arrhythmias, fibrosis of the heart, valve defects, and atherosclerosis. In particular, an effective amount of an Mst1 inhibitor may be used in combination with one or more compound for treatment of cardiac disease or of atherosclerosis, including but not limited to a beta-blocker, nitrate, calcium channel antagonists, angiotensin-converting enzyme (ACE) inhibitors, an anti-platelet drug, diuretics, digoxin and antilipemic agents, agents which alter cholesterol or lipid metabolism.

In a particular aspect of the invention, the Mst1 inhibitor is a mutant Mst1 which acts as an antagonist of Mst1, particularly a dominant negative Mst1. In one such example, the Mst1 mutant is Mst1 (K59R). In a method of the invention, cardiac myocytes are transduced, transfected or infected with nucleic acid or vector containing nucleic acid encoding a mutant Mst1 which acts as a dominant negative to antagonize wild type and endogenous Mst1. By expression of dominant negative Mst1 in cardiac myocytes, apoptosis is blocked or reduced and cardiac disease is thereby treated or ameliorated.

The DNA sequences of Mst1 of use in the present invention or portions thereof, may be prepared with a variety of known vectors, particularly vectors capable of expressing such DNAs in animal cells, particularly in human cells. In one such embodiment, the vectors include those suitable for delivery to human cells, particularly to cardiac or heart cells, such as myocytes. Examples of such vectors include viral vectors such as adenovirus, or naked DNA vectors, for instance for injection or delivery to the heart wherein the DNA is then expressed. The present invention also includes the preparation of plasmids or viruses including such vectors, and the use of the DNA sequences to construct vectors expressing antisense RNA, small interfering RNAs or ribozymes which would attack or interfere with the mRNAs of any or all of the DNA sequences encoding native or endogenous Mst1. Correspondingly, the preparation of antisense RNA, siRNAs and ribozymes are included herein.

In a further object, the invention provides animal models, including transgenic models, of cardiac disease and cardiac myopathy. Such animal models include transgenic animals expressing enhanced amounts of Mst1 or altered Mst1 (including wherein Mst1 is substantially more active or constitutively active). These animals are useful in studies of cardiac disease, including for the screening and assessment of potential cardiotherapeutic compounds. These animals include but are not limited to rats, mice, pigs, chicken, cows, monkeys, rabbits, sheep and dogs.

Other objects and advantages will become apparent to those skilled in the art from a review of the following description which proceeds with reference to the following illustrative drawings.

DETAILED DESCRIPTION

Figure 1A:
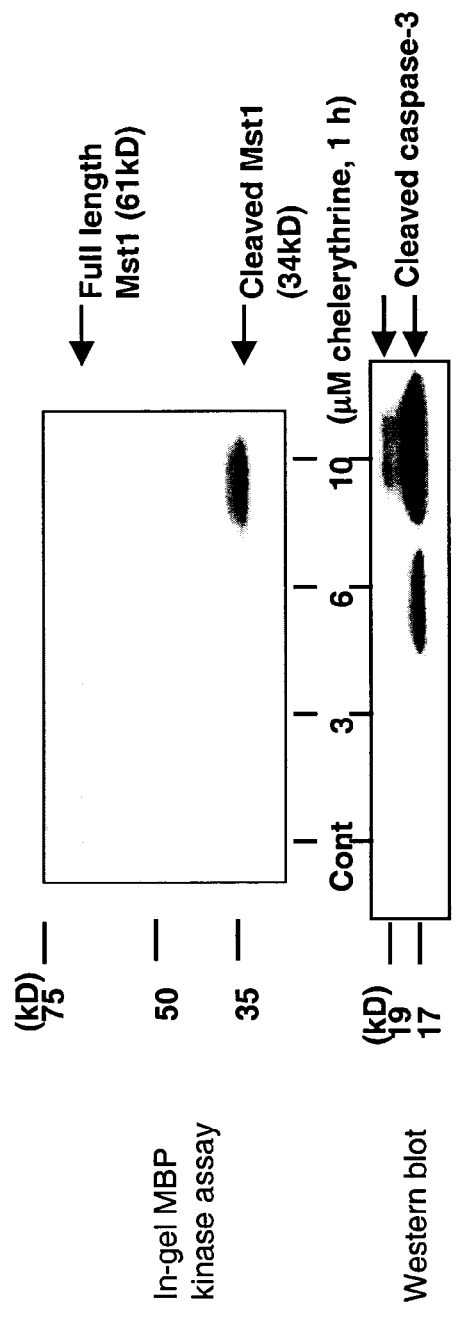
FIGS. 1A, 1B, 1C, 1D and 1E depict Mst1 activity assessed on treatment of cardiac myocytes with chelerythrine (Chele) or calyculin A. (A) Cardiac myocytes were treated with indicated concentrations of chelerythrine for 1 h. Cell lysates were subjected to in-gel myelin basic protein (MBP) kinase assay as well as immunoblotting with anti-cleaved caspase-3 antibody. Results are representative of more than five experiments. (B) Cardiac myocytes were treated with chelerythrine (Chele). In the right panel, myocytes were transduced with either control virus or adenovirus harboring XIAP 48 hours before Chele application. Cell lysates were subjected with immune complex in-gel MBP kinase assays, using anti-Mst1 polyclonal antibody (pAb-15). The activity of cleaved Mst1 is shown. (C) Cardiac myocytes were treated with Chele for the indicated durations. Immunoblot analyses were conducted by using anti-Mst1 monoclonal antibody (upper panel) and anti-Mst1 polyclonal antibody (lower panel), which detects the full length form and cleaved form (amino-terminal half) of Mst1, respectively. (D) Cardiac myocytes were subjected to 8 h of hypoxia alone (H) or 8 h hypoxia plus 12 h of reoxygenation (H/R). In-gel MBP kinase assays were performed. Control, C. Upper arrow indicates the full length form of Mst1, while lower arrow cleaved form of Mst1. (E) Cardiac myocytes were treated with vehicle (lane 1) or calyculin A (1 μM, lane 2). In-gel MBP kinase assays were performed. Arrow indicates the full length form of Mst1.

The studies provided herein assessed whether or not Mst1 plays an essential role in mediating apoptosis in cardiac myocytes, by using both cultured cardiac myocytes in vitro and transgenic mouse models in vivo. The results demonstrate that Mst1 is activated not only by genotoxic compounds but also by clinically relevant pathologic insults in the heart. Stimulation of or enhanced expression of Mst1 causes cardiac myocyte apoptosis and dilated cardiomyopathy, without any compensatory cardiac myocyte hypertrophy. In addition, specific inhibition of endogenous Mst1 by dominant negative Mst1 inhibits cardiac myocyte apoptosis and myocardial infarction in response to ischemia/reperfusion (I/R). Inhibition of endogenous Mst1 also inhibits the negative cardiac effects of cardiotoxic drugs, as demonstrated in blockage of doxorubicin-induced cardiomyopathy. In addition, on inhibition of endogenous Mst1, the cardiac dilation and cardiac dysfunction following myocardial infarction are significantly reduced. Thus, Mst1 plays an essential role in mediating apoptosis by clinically relevant pathologic stimuli in the heart and represents an important therapeutic target in ischemic heart diseases.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "mammalian sterile 20-like kinase-1", "Mst1" and any variants not specifically listed, may be used herein interchangeably, and as used throughout the present application and claims refer to proteinaceous material including single or multiple proteins, and extends to those proteins having the profile of activities set forth herein and in the claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "mammalian sterile 20-like kinase-1", "Mst1" and "Mst1(s)" are intended to include within their scope proteins specifically recited herein as well as all substantially homologous analogs and allelic variations. The protein and encoding nucleic acid sequences of Mst1 are publicly known and described including in the Genbank database.

The amino acid residues described herein are preferred to be in the "L" isomeric form. However, residues in the "D" isomeric form can be substituted for any L-amino acid residue, as long as the desired fuctional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, J. Biol. Chem., 243:3552–59 (1969), abbreviations for amino acid residues (for example for tyrosine, the 1-abbreviation Y, or the 3-letter abbreviation Tyr) are as well known and recognized in the art.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. Transcriptional and translational control sequences are DNA regulatory sequences, such as promoters, enhancers, polyadenylation signals, terminators, and the like, that provide for the expression of a coding sequence in a host cell.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers or oligonucleotides herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. It should be appreciated that also within the scope of the present invention are DNA sequences encoding which code for a having the same amino acid sequence as SEQ ID NO:, but which are degenerate to SEQ ID NO:. By "degenerate to" is meant that a different three-letter codon is used to specify a particular amino acid. It is well known in the art that specific and particular codons can be used interchangeably to code for each specific amino acid.

Mutations can be made in Mst1 or the compounds of the present invention such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include seguences containing conservative changes which do not significantly alter the activity or binding characteristics of the resulting protein.

The following is one example of various groupings of amino acids:

Amino Acids with Nonpolar R Groups
Alanine, Valine, Leucine, Isoleucine, Proline, Phenylalanine, Tryptophan Methionine Amino Acids with Uncharged Polar R Groups
Glycine, Serine, Threonine, Cysteine, Tyrosine, Asparagine, Glutamine Amino Acids with Charged Polar R Groups (Negatively Charged at Ph 6.0)
Aspartic acid, Glutamic acid Basic Amino Acids (Positively Charged at pH 6.0)
Lysine, Arginine, Histidine (at pH 6.0)

Another grouping may be those amino acids with phenyl groups: Phenylalanine, Tryptophan, Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces –turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

"Heart failure" refers to the incapacity of the heart to assume a normal contractile function.

"Treat and treatment" refer to both therapeutic treatment and prophylactic or preventative measures, wherein the object is to prevent or slow down (lessen) an undesired physiological condition, disorder or disease or obtain beneficial or desired clinical results. For purposes of this invention, beneficial or desired clinical results include, but are not limited to, alleviation of symptoms; diminishment of extent of condition, disorder or disease; stabilized (i.e. not worsening) state of condition, disorder or disease; delay or slowing of condition, disorder, or disease progression; amelioration of the condition, disorder or disease state, remission (whether partial or total), whether detectable or undetectable; or enhancement or improvement of condition, disorder or disease. Treatment includes eliciting a cellular response that is clinically significant, without excessive levels of side effects. Treatment also includes prolonging survival as compared to expected survival if not receiving treatment.

The phrase "pharmaceutically acceptable" refers to molecular entities and compositions that are physiologically tolerable and do not typically produce an allergic or similar untoward reaction, such as gastric upset, dizziness and the like, when administered to a human.

"Pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Parenteral" refers to introduction of the polypeptide by intravenous, intraarterial, intraperitoneal, intramuscular, intraventricular, intracranial, subcutaneous, subdermal, transvaginal, oral, nasal or rectal routes.

"Mammal" refers to any animal classified as a mammal, including humans, domestic and farm animals, and zoo, sports and pet companion animals such as a household pet and other domesticated animal such as, but not limited to, cattle, sheep, ferrets, swine, horses, poultry, rabbits, goats, dogs, cats, and the like. Preferred companion animals are dogs and cats. Preferably, the mammal is human.

"Patient" refers to a mammal, preferably a human, in need of treatment of a condition, disorder or disease.

"Inhibitor" includes but is not limited to, any suitable molecule, compound, protein or fragment thereof, nucleic acid, formulation or substance that can regulate Mst1 activity in such a way that Mst1 is decreased or wherein the effects of Mst1 are blocked or altered. The inhibitor includes an antagonist of Mst1, particularly an Mst1 mutant or altered form that acts as a dominant negative. An inhibitor of the Mst1 pathway includes any substance that alters the effect of Mst1 at the level downstream or upstream of Mst1. These include downstream proteins capable of being modulated, including activated, by a signal from Mst1 or which are more active on a signal from Mst1 or in the presence of phosphorylated Mst1 or increased relative levels of cleaved Mst1. Mst1 pathway further includes the upstream proteins, including particulary a kinase(s), which are capable of phosphorylating amino acid(s) on Mst1 or involved in the signal which results in phosphorylated Mst1 or activated, cleaved Mst1. Exemplary downstream proteins include but are not limited to caspase and myelinbasic protein. The inhibitor can include, but is not limited to the specifically identified Caspase 3, Calyculin A and Chelerythrine. The inhibitor includes compounds which block Mst1 expression, including transcription or translation, such as antisense nucleic acids, siRNAs and ribozymes.

As used herein, "pg" means picogram, "ng" means nanogram, "ug" or "µg" mean microgram, "mg" means milligram, "ul" or "µl" mean microliter, "ml" means milliliter, "l" means liter.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20$^N$C below the predicted or determined $T_m$ with washes of higher stringency, if desired.

Screening Methods and Assays

Once a compound that binds to Mst1 or otherwise modulates the Mst1 pathway is selected, it can be tested for its ability to modulate cardiac myocyte apoptosis or function. The effect of compounds on cardiac myocyte apoptosis can also be tested in vivo. Cardiac function and output can be measured in vivo in animals by methods and assays well known in the art, including as described herein. In one such example of this assay, including as described herein, a myocardial infarction is generated in animal by ligation of the left coronary artery and the animals are then observed for cardiac myopathy and cardiac function.

The function of cardiac myocytes and status of the Mst1 pathway may be determined by assessing the activation of intracellular proteins indicative of apoptosis and/or Mst1 activation, particularly including, but not limited to, proteins or kinases such as caspase, Mst1 cleavage status, MAPK, JNK, etc. which may be substrates for Mst1 or activated or more active in the presence of phosphorylated or cleaved Mst1, or active on initiation of apoptosis. In addition, the activation of Mst1 or phosphorylation of Mst1 or its substrate, including MBP, may be assessed. Thus, following the incubation of cardiac myocytes or other cells expressing Mst1 with a test compound, the cells are lysed and their intracellular contents subjected to the appropriate tests, such as Western blots, kinase assays, and electrophoretic mobility gel shift assays (EMSAs).

In one embodiment, the modulation comprises phosphorylation of intracellular proteins in the Mst1 pathway, and more preferably of kinases, particularly including Mst1. The methods of the present invention may utilize any of the appropriate assays available in the art for determining whether a kinase has been phosphorylated. Preferably, the assays used are Western blots or kinase assays.

In an embodiment, methods for screening cardiotherapeutic compounds based on their ability to activate phosphatase (s) (partially or completely) are also provided herein. The compounds to be screened may include compounds that bind to Mst1 or dephopsphorylate Mst1, and methods for selecting such compounds are described above. The phosphatases inhibit the kinases specific for cardiac myocyte apoptosis and/or function, including Mst1 and proteins (kinases) in the Mst1 pathway which may be substrates for Mst1 or activated or more active in the presence of phosphorylated Mst1, e.g. caspase. Preferably, the phosphatases are Mst1 specific or Mst1 pathway specific. While not being bound to a particular theory, this method is feasible for this purpose due to the fact that in some instances a kinase activity is tightly regulated by its corresponding phosphatase. In case of ERK1/2, the phosphatases are known as the mitogen activated protein kinases phosphatase-1,2,3 (MKP-1,2,3). These phosphatases belong to a family of dual specificity phosphatases, which are responsible for the removal of phosphate groups from the threonine and tyrosine residues on their corresponding kinases (Camps et al., FASEB J., 14, pp. 6–16, 1999). The prompt removal of phosphate groups by phosphatases ensures that kinase activation is short-lived and that the level of phosphorylation is low in a resting cell. However, in order for the phosphatase to be active and remove phosphate groups, it also needs to be phosphorylated. Therefore, activation of phosphatase activity results in inactivation of kinase activity. The ability of the test compounds to activate phosphatase(s) can be determined by performing Western blots or kinase assays. See above. For additional details on assessing phosphatase activity, see Muda et al., J Biol Chem., 273:9323–9329, 1998, and Camps et al., Science 280:1262–1265, 1998. If the compound is determined to possess enhanced phosphatase activity, it can further be tested in one of the cardiac myocyte apoptosis or in vitro or in vivo assays to determine its effect on cardiac function and/or cardiomyopathy.

In a further embodiment of this invention, commercial test kits suitable for use by a medical specialist may be prepared to determine the presence or absence of or the amount of Mst1 or Mst1 activity in cells. Accordingly, one class of such kits will contain at least the labeled Mst1 or its binding partner, for instance an antibody specific thereto, and directions, of course, depending upon the method selected, e.g., competitive, sandwich, and the like, all and any of which are methods well known to the skilled artisan. The kits may also contain peripheral reagents such as buffers, stabilizers, etc.

Accordingly, a test kit may be prepared for the demonstration of the presence or capability of cells for Mst1 activity, comprising:

(a) a predetermined amount of at least one labeled immunochemically reactive component obtained by the direct or indirect attachment of Mst1 or a specific binding partner thereto, to a detectable label;
(b) other reagents; and
(c) directions for use of said kit.

More specifically, the diagnostic test kit may comprise:
(a) a known amount of Mst1 as described above (or a binding partner) generally bound to a solid phase to form an immunosorbent, or in the alternative, bound to a suitable tag, or plural such end products, etc. (or their binding partners) one of each;
(b) if necessary, other reagents; and
(c) directions for use of said test kit.

In a further variation, the test kit may be prepared and used for the purposes stated above, which operates according to a predetermined protocol (e.g. competitive, sandwich, double antibody, etc.), and comprises:
(a) a labeled component which has been obtained by coupling Mst1 to a detectable label;
(b) one or more additional immunochemical reagents of which at least one reagent is a ligand or an immobilized ligand, which ligand is selected from the group consisting of:
  (i) a ligand capable of binding with the labeled component (a);
  (ii) a ligand capable of binding with a binding partner of the labeled component (a);
  (iii) a ligand capable of binding with at least one of the component(s) to be determined; and
  (iv) a ligand capable of binding with at least one of the binding partners of at least one of the component(s) to be determined; and
(c) directions for the performance of a protocol for the detection and/or determination of one or more components of an immunochemical reaction between Mst1 and a specific binding partner thereto.

Compounds and Agents

Examples of agents, candidate compounds or test compounds include, but are not limited to, nucleic acids (e.g., DNA and RNA), carbohydrates, lipids, proteins, peptides, peptidomimetics, small molecules and other drugs. In one preferred aspect, agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683).

Phage display libraries may be used to screen potential Mst1 modulators. Their usefulness lies in the ability to screen, for example, a library displaying a billion different compounds with only a modest investment of time, money, and resources. For use of phage display libraries in a screening process, see, for instance, Kay et al., Methods, 240–246, 2001. An exemplary scheme for using phage display libraries to identify compounds that bind or interact with Mst1 may be described as follows: initially, an aliquot of the library is introduced into microtiter plate wells that have previously been coated with target protein, e.g. Mst1. After incubation (e.g. 2 hrs), the nonbinding phage are washed away, and the bound phage are recovered by denaturing or destroying the target with exposure to harsh conditions such as, for instance pH 2, but leaving the phage intact. After transferring the phage to another tube, the conditions are neutralized, followed by infection of bacteria with the phage and production of more phage particles. The amplified phage are then rescreened to complete one cycle of affinity selection. After three or more rounds of screening, the phage are plated out such that there are individual plaques that can be further analyzed. For example, the conformation of binding activity of affinity-purified phage for Mst1 may be obtained by performing ELISAs. One skilled in the art can easily perform these experiments. In one aspect, an Mst1 molecule used for any of the assays may be selected from a recombinant Mst1 protein, an Mst1 fusion protein, an analog, derivative, or mimic thereof. In a preferred aspect, Mst1 is a recombinant Mst1 protein.

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented, e.g., presented in solution (e.g., Houghten, 1992, Bio/Techniques 13:412–421), or on beads (Lam, 1991, Nature 354:82–84), chips (Fodor, 1993, Nature 364:555–556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865–1869) or phage (Scott and Smith, 1990, Science 249:386–390; Devlin, 1990, Science 249:404–406; Cwirla et al., 1990, Proc. Natl. Acad. Sci. USA 87:6378–6382; and Felici, 1991, J. Mol. Biol. 222: 301–310).

Antibodies, including polyclonal and monoclonal antibodies, particularly anti-Mst1 antibodies and neutralizing antibodies may be useful as compounds to modulate cardiac myocyte apoptosis and/or function. Also, antibodies including both polyclonal and monoclonal antibodies, and drugs that modulate the activity of Mst1 and/or their subunits may possess certain diagnostic applications and may for example, be utilized for the purpose of detecting and/or measuring conditions such as cardiac disease, cardiomyopathy, or cardiac function. Mst1 or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity (ies) of Mst1 may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against Mst1 peptides can be screened for various properties; i.e., isotype, epitope, affinity, etc. Of particular interest are monoclonal antibodies that neutralize the activity of Mst1. Such monoclonals can be readily identified in Mst1 activity assays, for instance in kinase assays using MBP as substrate.

Once an Mst1 modulating compound has been optimally designed, for example as described above, substitutions may then be made in some of its atoms or chemical groups in order to improve or modify its binding properties, or its pharmaceutical properties such as stability or toxicity. Generally, initial substitutions are conservative, i.e., the replacement group will have approximately the same size, shape, hydrophobicity and charge as the original group. One of skill in the art will understand that substitutions known in the art to alter conformation should be avoided. Such altered chemical compounds may then be analyzed for efficiency of modulating Mst1, including in assays as described herein.

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. The preparation of pharmaceutically acceptable isomers, solvates or hydrates would be apparent to one of ordinary skill in the art.

Mathods and Therapeutic and Pharmaceutical Compositions

The Mst1 modulators of the present invention, particularly Mst1 inhibitors, may be prepared in pharmaceutical compositions, with a suitable carrier and at a strength effective for administration by various means to a patient experiencing cardiac disease, including cardiomyopathy or compromised cardiac function, for the treatment or amelioration thereof. A variety of administrative techniques may be utilized, among them parenteral techniques such as subcutaneous, intravenous and intraperitoneal injections, catheterizations and the like. Average quantities of the modulators or their subunits may vary and in particular should be based upon the recommendations and prescription of a qualified physician or veterinarian.

A pharmaceutical composition useful in the present invention comprises an Mst1 inhibitor (such as described above) and a pharmaceutically acceptable carrier, excipient, diluent and/or salt. Pharmaceutically acceptable carrier, diluent, excipient and/or salt means that the carrier, diluent, excipient and/or salt must be compatible with the other ingredients of the formulation, does not adversely affect the therapeutic benefit of the Mst1 inhibitor, and is not deleterious to the recipient thereof.

In a preferred embodiment of the invention, a method of treating or ameliorating cardiac disease is provided by administering compositions comprising compounds identified by the screening methods provided herein. The Mst1 modulating compositions of the present invention may be utilized by providing an effective amount of such compositions to a subject in need thereof.

The invention provides a method for treating cardiac disease in a mammal comprising administering to said mammal an effective amount of an Mst1 inhibitor. In a particular aspect, the invention further provides a method for treating a cardiac disease or dysfunction selected from the group of congestive heart failure, cardiomyopathy, including ischemic and nonischemic cardiomyopathy, coronary artery disease, arrhythmias, fibrosis of the heart, valve defects, and atherosclerosis in a mammal comprising administering to said mammal an effective amount of an Mst1 inhibitor. In a still further aspect a method is provided for reducing the risk of cardiomyopathy or dysfunction in a mammal after said mammal has suffered a myocardial infarct or other coronary event wherein blood flow to the heart is compromised or significantly reduced comprising administering to said mammal an effective amount of an Mst1 inhibitor or Mst1 pathway inhibitor. In an additional aspect, the invention provides a method of cardioprotection, wherein an inhibitor of Mst1 is administered in conjunction with or following therapy with a compound or drug which is cardiotoxic or has potential to be cardiotoxic. In this method, an Mst1 modulator blocks or otherwise reduces the cardiotoxic effects of a drug or compound. In a particular embodiment, the drug or compound is a chemotherapeutic agent, particularly an anticancer agent, including but not limited to doxorubicin. In a further aspect, administration of the Mst1 modulator enables chemotherapeutic, particularly anti-cancer or anti-tumor compounds, treatment without significant cardiotoxic effects or permits prolonged chemotherapy or administration of higher concentrations or amounts of a potentially cardiotoxic drug.

In general, for use in treatment, the compounds of the invention may be used alone or in combination with other compositions for the treatment of heart disease, including but not limited to congestive heart failure, cardiomyopathy, including ischemic and nonischemic cardiomyopathy, coronary artery disease, arrhythmias, fibrosis of the heart, valve defects, and atherosclerosis. In particular, an effective amount of an Mst1 inhibitor may be used in combination with one or more compound for treatment of cardiac disease or of atherosclerosis, including but not limited to a beta-blocker, nitrate, calcium channel antagonists, angiotensin-converting enzyme (ACE) inhibitors, an anti-platelet drug, diuretics, digoxin and antilipemic agents, agents which alter cholesterol or lipid metabolism. Further examples of such or treatmantilipemic agents include, but are not limited to the statins, such as Lovastatin (Mevacor®), Atorvastatin (Lipitor®), Simvastatin (Zocor®), Cerivastatin (Baycol®), Pravastatin (Pravacol®), Fluvastatin (Lescol®) and Rosuvastatin; as well as other classes of compounds including cholesterol ester transfer protein inhibitors; cholesterol adsorption inhibitors (e.g., Ezetimide®); fibrates (e.g., Gemfibrozil®); nicotinic acid (e.g., niacin and analogs, Niaspan®); bile acid reuptake inhibitors; and modulators of nuclear hormone receptors such as PPARa, PPARb, PPARg, LXRa, LXRb, FXR, RORa and SHP.

Administration of the compounds or pharmaceutical compositions thereof for practicing the present invention can be by any method that delivers the compounds systemically. These methods include oral routes, parenteral routes, intraduodenal routes, etc.

For topical applications, the compound or pharmaceutical composition thereof can be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax, sugars such as lactose and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Depending on the particular condition, disorder or disease to be treated, additional therapeutic agents can be administered together with the Mst1 inhibitor. Those additional agents can be administered sequentially in any order, as part of a multiple dosage regimen, from the Mst1 inhibitor-containing composition (consecutive or intermittent administration). Alternatively, those agents can be part of a single dosage form, mixed together with the Mst1 inhibitor in a single composition (simultaneous or concurrent administration).

For oral administration, a pharmaceutical composition useful in the invention can take the form of solutions, suspensions, tablets, pills, capsules, powders, granules, semisolids, sustained release formulations, elixirs, aerosols, and the like. Tablets containing various excipients such as sodium citrate, calcium carbonate and calcium phosphate are employed along with various disintegrants such as starch, preferably potato or tapioca starch, and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The term "parenteral" as used herein refers to modes of administration, which include intravenous, intramuscular, intraperitoneal, intrastemal, subcutaneous, intramedullary and intraarticular injection and infusion. A pharmaceutical composition for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Aqueous solutions are especially suitable for intravenous, intramuscular, subcutaneous and intraperitoneal injection purposes. In this connection, the sterile aqueous media employed are all readily obtainable by standard techniques well-known to those skilled in the art. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical compositions useful in the present invention can also contain adjuvants such as, but not limited to, preservatives, wetting agents, emulsifying agents, and dispersing agents. Prevention of the action of microorganisms can be ensured by the inclusion of various antibacterial and antifungal agents, such as for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents that delay absorption such as aluminum monostearate and gelatin.

In some cases, in order to prolong the effect of the drugs, it is desirable to slow the absorption from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide, polyglycolide, and polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Administration by slow infusion is particularly useful when intrathecal or epidural routes are employed. A number of implantable or body-mountable pumps useful in delivering compound at a regulated rate are known in the art. See, e.g., U.S. Pat. No. 4,619,652.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

For purposes of transdermal (e.g., topical) administration, dilute sterile, aqueous or partially aqueous solutions (usually in about 0.1% to 5% concentration), otherwise similar to the above parenteral solutions, are prepared.

The pharmaceutical compositions useful in the invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In nonpressurized powder compositions, the active ingredients in finely divided form can be used in admixture with a larger-sized pharmaceutically acceptable inert carrier comprising particles having a size, for example, of up to 100 μm in diameter. Suitable inert carriers include sugars such as lactose. Desirably, at least 95% by weight of the particles of the active ingredient have an effective particle size in the range of 0.01 to 10 μm.

Alternatively, the composition can be pressurized and contain a compressed gas, such as, e.g., nitrogen, carbon dioxide or a liquefied gas propellant. The liquefied propellant medium and indeed the total composition are preferably such that the active ingredients do not dissolve therein to any substantial extent. The pressurized composition can also contain a surface active agent. The surface active agent can be a liquid or solid non-ionic surface active agent or can be a solid anionic surface active agent. It is preferred to use the solid anionic surface active agent in the form of a sodium salt.

Compositions for rectal or vaginal administration are preferably suppositories which can be prepared by mixing the compounds of the invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions useful in the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (see e.g., Prescott, E., Meth. Cell Biol. 14:33 (1976)).

Other pharmaceutically acceptable carrier includes, but is not limited to, a non-toxic solid, semisolid or liquid filler, diluent, encapsulating material or formulation auxiliary of any type, including but not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solid pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Methods of preparing various pharmaceutical compositions with a certain amount of active ingredient are known, or will be apparent in light of this disclosure, to those skilled in this art. Other suitable pharmaceutical excipients and their formulations are described in Remington's Pharmaceutical Sciences, edited by E. W. Martin, Mack Publishing Company, 19th ed. (1995).

Pharmaceutical compositions useful in the present invention can contain 0.1%–95% of the compound(s) of this invention, preferably 1%–70%. In any event, the composition or formulation to be administered will contain a quantity of a compound(s) according to this invention in an amount effective to treat the condition, disorder or disease of the subject being treated.

One of ordinary skill in the art will appreciate that pharmaceutically effective amounts of the Mst1 inhibitor can be determined empirically and can be employed in pure form or, where such forms exist, in pharmaceutically acceptable salt, ester or prodrug form. The agents can be administered to a patient as pharmaceutical compositions in combination with one or more pharmaceutically acceptable excipients. It will be understood that, when administered to, for example, a human patient, the total daily usage of the agents or composition of the present invention will be decided within the scope of sound medical judgement by the attending physician. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

For example, satisfactory results are obtained by oral administration of the compounds at dosages on the order of from 0.05 to 500 mg/kg/day, preferably 0.1 to 100 mg/kg/day, more preferably 1 to 50 mg/kg/day, administered once or, in divided doses, 2 to 4 times per day. On administration parenterally, for example, by i.v. bolus, drip or infusion, dosages on the order of from 0.01 to 1000 mg/kg/day, preferably 0.05 to 500 mg/kg/day, and more preferably 0.1 to 100 mg/kg/day, can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging can also be arranged in a patient specific manner to provide a predetermined concentration of the agents in the blood, as determined by techniques accepted and routine in the art (HPLC is preferred). Thus patient dosaging can be adjusted to achieve regular on-going blood levels, as measured by HPLC, on the order of from 50 to 5000 ng/ml, preferably 100 to 2500 ng/ml.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog-, -modulator or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of~binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the Mst1 antagonist or analog or modulator thereof, and one or more of the following active ingredients, including but not limited to: an antibiotic, a steroid, an anticoagulant, a statin or other cholesterol lowering drug, an anti-hypertensive drug, an immune modulatory drug.

Another feature of this invention is the expression of the DNA sequences disclosed herein, including Mst1, particularly altered, including dominant negative forms of Mst1. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAS, e.g., the numerous derivatives of phage □, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage □, the control regions of fd coat protein, the promoter for 3-phosphoglycerate kinase or other glycolytic enzymes, the promoters of acid phosphatase (e.g., Pho5), the promoters of the yeast—mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will enable expression the DNA sequences encoding Mst1 or an antagonist of Mst1, including for example a mutant and dominant negative Mst1, of this invention on transduction to animal cells, on infection of animal cells, or on fermentation or in large scale animal culture.

It is further intended that Mst1 analogs may be prepared from nucleotide sequences of the protein complex/subunit derived within the scope of the present invention. Analogs, such as fragments, may be produced, for example, by pepsin or other protease digestion of Mst1 polypeptide. Other analogs, such as muteins, can be produced by standard site-directed mutagenesis of Mst1 coding sequences. Analogs exhibiting "Mst1 activity", including kinase activity, such as small molecules, whether functioning as promoters or inhibitors, may be identified by known in vivo and/or in vitro assays.

As mentioned above, a DNA sequence encoding Mst1 or an analog, including a dominant negative mutant of Mst1, can be prepared synthetically rather than cloned. The DNA sequence can be designed with the appropriate codons for the Mst1 amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature,* 292:756 (1981); Nambair et al., *Science,* 223:1299 (1984); Jay et al., *J. Biol. Chem.,* 259: 6311 (1984). Synthetic DNA sequences allow convenient construction of genes which will express Mst1 analogs or "muteins". Alternatively, DNA encoding muteins can be made by site-directed mutagenesis of native Mst1 genes or cDNAs, and muteins can be made directly using conventional polypeptide synthesis. A general method for site-specific incorporation of unnatural amino acids into proteins is described in Christopher J. Noren, Spencer J. Anthony-Cahill, Michael C. Griffith, Peter G. Schultz, *Science,* 244: 182–188 (April 1989). This method may be used to create analogs with unnatural amino acids.

The present invention extends to the preparation of antisense oligonucleotides, small interfering RNAs (siRNAs), and ribozymes that may be used to interfere with the expression of Mst1 at the translational level. This approach utilizes antisense nucleic acid and ribozymes to block translation of a specific mRNA, either by masking that mRNA with an antisense nucleic acid, destabilizing it or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into Mst1-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, *Tetrahymena*-type and "hammerhead"-type. (Hasselhoff and Gerlach, 1988) *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for Mst1.

The use of RNA interference strategies to inhibit the expression of Mst1 is further embodied in the invention. Thus, methods of RNA interference and small interfering RNA compositions are included in the methods and compositions of the present invention. RNA interference refers to the silencing of genes specifically by double stranded RNA (dsRNA) (Fine, A. et al (1998) Nature 391;806–811). In one embodiment, short or small interfering RNA (siRNA) is utilized (Elbashir, S. M. et al (2001) Nature 411:494–498). In addition, long double stranded RNA hairpins may be employed (Tavernarakis, N. et al (2000) Nature Genet 24:180–183; Chuang, C. F. and Meyerowitz, E. M. (2000) PNAS USA 97:4985–90; Smith, NA et al (2000) Nature 407:319–20). Virus-mediated RNA interference against K-Ras has been described (B rummelkamp, T. R. et al (2002) Cancer Cell 2:243–247).

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

The studies described herein were undertaken to determine whether or not Mst1 plays an essential role in mediating apoptosis in cardiac myocytes, by using both cultured cardiac myocytes in vitro and transgenic mouse models in vivo. The results demonstrate that Mst1 is activated not only by genotoxic compounds but also by clinically relevant pathologic insults in the heart. Stimulation of Mst1 causes cardiac myocyte apoptosis and dilated cardiomyopathy without any compensatory cardiac myocyte hypertrophy. Furthermore, specific inhibition of endogenous Mst1 by dominant negative Mst1 inhibits cardiac myocyte apoptosis and myocardial infarction in response to I/R. These results indicate that Mst1 plays an essential role in mediating apoptosis by clinically relevant pathologic stimuli in the heart and identify Mst1 as an important therapeutic target in ischemic heart diseases.

Mst1 is a Predominant MBP Kinase Activated by Potent Proapoptotic Stimuli in Cardiac Myocytes Our results suggest that Mst1 is a prominent MBP kinase activated by potent apoptotic stimuli, including chelerythrine and calyculin A, in cardiac myocytes. Activation of Mst1 was also observed in response to hypoxia/reoxygenation of cardiac myocyte in vitro and I/R of the mouse heart in vivo. Activation of Mst1 by such clinically relevant stresses has not been reported previously. Overexpression of wild type Mst1 was sufficient to cause typical findings of apoptosis, including cell shrinkage, cytoplasmic accumulation of mono- and oligo-nucleosomes and activation of caspase-3 in cardiac myocytes. Cell death induced by wild type Mst1 was suppressed in the presence of the caspase-3 inhibitor. These results suggest that activation of Mst1 activates caspase-3, which in turn mediates cardiac myocyte apoptosis. Since cleavage and activation of Mst1 were at least in part inhibited by the caspase inhibitors, activation of Mst1 partially depends upon caspases. Thus, Mst1 and caspase-3 stimulate one another, thereby initiating a positive feed back mechanism leading to increased apoptosis in cardiac myocytes. These results suggest that Mst1 can be an important regulator of apoptosis in cardiac myocytes. This notion is also well supported by the fact that cardiac myocyte apoptosis by chelerythrine or calyculin A treatment as well as in response to I/R was significantly suppressed in the presence of dominant negative Mst1.

Recent evidence suggests that Mst1 is activated either by phosphorylation of the catalytic domain or by caspase-mediated cleavage of the C-terminal inhibitory domain (42). In fact, Mst1 is activated by both mechanisms in cardiac myocytes: chelerythrine causes activation of Mst1 via caspase-dependent cleavage, while calyculin A causes activation of the full length form of Mst1 possibly through phosphorylation. Since both mechanisms cause myocyte death, which was inhibited by dominant negative Mst1, activation of Mst1 by either mechanism causes cardiac myocyte apoptosis. In this regard, it would be interesting to determine, by using a cleavage resistant form of Mst1, if the cleaved form and the full-length form of Mst1 cause apoptosis with distinct morphological characteristics. Interestingly, the active form of Mst1 in Tg-Mst1 or in control mice subjected to I/R predominantly exists in the full length form. This indicates that cleavage of Mst1 by preceded activation of caspase-3 may not be required for activation of Mst1 in pathological conditions in vivo. Since partial cleavage of Mst1 was observed when higher doses of AdX-Mst1 were transduced in cardiac myocytes in vitro or I/R was applied to Tg-Mst1 (data not shown), we speculate that higher levels of caspase activation is required for the cleavage of Mst1 to be seen. Since we could detect cleavage of caspase-3 even without cleavage of Mst1 in Tg-Mst1, caspase 3 may have a higher affinity for self-cleavage compared with cleavage of Mst1. Alternatively, activation of caspase-3 and cleavage of Mst1 could co-exist at the time only when cells are undergoing apoptosis, but anti-cleaved caspase-3 antibody may be more sensitive for detection of the cleaved product.

The pattern of Mst1 activation by overexpression or by I/R is analogous to that by calyculin A, a phosphatase inhibitor. In this regard, it will be interesting to examine if the activation loop of Mst1 is phosphorylated in Tg-Mst1 or in response to I/R (42). It has been reported that transgenic mice overexpressing an inhibitor of PP-2A exhibited dilated cardiomyopathy (43). It would be interesting to examine if the activation of Mst1 is involved in development of heart failure in these animals.

Cardiac Specific Overexpression of Mst1 Stimulates Cardiac Myocyte Apoptosis and Induces Dilated Cardiomyopathy Cardiac specific overexpression of wild type Mst1 caused dilation in all 4 chambers, wall thinning, and reduced bi-ventricular function, consistent with findings of dilated cardiomyopathy. Interestingly, hypertrophy of surviving ventricular cardiac myocytes was not observed. To our knowledge, Mst1 is unique among protein kinases thus far overexpressed in the mouse heart in vivo, because overexpression of Mst1 in the heart primarily causes dilated cardiomyopathy without inducing cardiac myocyte hypertrophy. It should be noted that although cardiac function was generally reduced, some variability was observed in the severity of congestive heart failure among transgenic littermate. This suggests that other genetic modifiers may exist to regulate the susceptibility of mice to congestive heart failure.

We asked what is the cause of dilated cardiomyopathy in Tg-Mst1? We found that Tg-Mst1 have an increased number of TUNEL positive cells, which was accompanied by increased levels of caspase-3 activity. Although whether the TUNEL positive cells in Tg-Mst1 represent apoptosis or oncosis remains to be elucidated, since Mst1 promotes cell death consistent with apoptosis in vitro, it is likely that Tg-Mst1 mice have more apoptosis. Considering the fact that increases in TUNEL positive myocytes and interstitial fibrosis were observed even before the animals manifest overt sign of heart failure, increases in apoptosis may be the primary cause of dilated cardiomyopathy. This notion is also supported by the fact that contraction and relaxation function of single cardiac myocytes isolated from Tg-Mst1 with decreased LVEF were preserved. Thus, we propose that decreases in the number of total cardiac myocytes in the heart (due to increases in apoptosis) at least in part may contribute to initial development of dilated cardiomyopathy in Tg-Mst1.

It has been suggested that Mst1 is a MAP4K and regulates downstream stress activated protein kinases, such as JNK and p38. The activated form of Mst1 is translocated to the nucleus and potentially affects nuclear components of the apoptosis machinery, including ICAD (Inhibitor of Caspase-Activated DNase) (31,32,42). However, the targets of Mst1 mediating its proapoptotic effects in cardiac myocytes remain to be elucidated. Genomic analyses of Tg-Mst1 indicated that some components of nuclear encoded mitochondrial cytochrome c oxidase are downregulated. It has been shown that mitochondrial DNA encoded cytochrome c is downregulated in the failing mouse heart possibly due to DNA damage caused by increased levels of reactive oxygen species (44). It has been suggested that downregulation of cytochrome c oxidase causes severe impairment of mitochondrial ATP production as well as increased production of reactive oxygen species, a potent inducer of apoptosis (45). It should be noted that reduction of mRNA of some components of cytochrome c oxidase was observed in young Tg-Mst1 mice, which yet showed overt sign of congestive heart failure. Thus, we propose that downregulation of cytochrome c oxidase is at least in part involved in the pathogenesis of DCM in Tg-Mst1. It should be noted that downregulation of cytochrome c oxidase is not necessarily the common feature of congestive heart failure. Thus, this may be a unique downstream target of Mst1. The precise signaling mechanism connecting Mst1 and reduced cytochrome c oxidase expression remains to be elucidated.

Our results suggest that Mst1 is a MAP4K and regulates downstream SRPKs, such as p38-MAPK and p46-JNKs in cardiac myocytes. Whether or not p38-MAPK and/or p46-JNKs mediate proapoptotic effects of Mst1 is of great interest. The activated form of Mst1 is translocated to the nucleus and may affect Death-associated protein 4 (DAP4) (51) and the nuclear components of the apoptosis machinery, including ICAD (Inhibitor of Caspase-Activated DNase) (31, 32, 42). Although Mst1 efficiently phosphorylates MBP at least in vitro, patho-physiologically relevant substrates of Mst1, mediating the proapoptotic effect of Mst1, remain to be elucidated in cardiac myocytes.

Cardiac Specific Overexpression of Mst1 Prevents Compensatory Cardiac Myocyte Hypertrophy and Potentially Obscures Operation of the Frank-Starling Mechanism in Individual Cardiac Myocytes One of the most surprising findings in this study was that hypertrophy of surviving ventricular cardiac myocytes was not observed in Tg-Mst1. To our knowledge, Mst1 is unique among protein kinases thus far overexpressed in the mouse heart in vivo, because overexpression of Mst1 in the heart primarily stimulates cardiac myocyte death without compensatory hypertrophy. Absence of cardiac hypertrophy not only leaves the wall stress elevated but also fails to compensate for the loss of cardiac mass caused by apoptosis in Tg-Mst1. Importantly, the longitudinal length as well as the cell volume of isolated LV myocytes were significantly smaller in Tg-Mst1. Although increases in myocyte length are commonly observed in dilated cardiomyopathy, to our knowledge, decreases in cell volume or cardiac myocyte length in dilated cardiomyopathy have not been previously reported. We speculate that side-to-side slippage of cardiac myocytes (49), rather than elongation of individual myocytes, supports ventricular dilation in Tg-Mst1. Thus, increased tension development in dilated hearts according to the Frank-Starling would become less efficient at a single cell level in Tg-Mst1, which may further contribute to decreased cardiac function in these animals.

At present, we are not certain why compensatory cardiac myocyte hypertrophy does not take place in Tg-Mst1 despite elevated wall stress. Mst1 may inhibit signaling molecules causing hypertrophy through either direct phosphorylation or caspase-mediated cleavage. Little is known as to the cellular actions of Mst1 besides apoptosis. If Mst1 possess such direct anti-hypertrophic function, this would be a novel function of Mst1. Alternatively, ongoing cell proliferation could make cardiac myocytes smaller (17). In this regard, whether or not increased cell death stimulates myocyte proliferation in Tg-Mst1 remains to be elucidated.

Mst1 Plays an Important Role in Mediating Cardiac Myocyte Death in Response to I/R in the Heart Although endogenous Mst1 is activated by proapoptotic stimuli in both neonatal rat cardiac myocytes and adult mouse heart, one may argue that overexpression of Mst1 causes unphysiological responses. In order to address this issue, we tested the effect of dominant negative Mst1 (K59R) and confirmed that it was able to suppress the activity of endogenous Mst1 in baseline and in response to I/R. Most importantly, cardiac specific expression of dominant negative Mst1 significantly reduced the extent of myocardial infarction. Since increases in both TUNEL positive cells and DNA laddering by I/R were significantly suppressed in Tg-Mst1 (K59R), inhibition of endogenous Mst1 most likely reduced cardiac myocyte apoptosis. We cannot completely exclude the possibility that overexpression of Mst1 (K59R) may affect activities of other protein kinases. However, since Mst1 is a predominant MBP kinase activated by I/R, the effect of the Mst1 (K59R) is most likely mediated through inhibition of Mst1 or that of the closely related Mst 1 family. Our results clearly indicate that inhibition of Mst1 effectively reduces cardiac myocyte death by I/R. Mst1 and caspase stimulate one another, thereby forming a positive feedback loop. Thus, inhibiting the key molecule facilitating this amplification loop would effectively block promotion of apoptosis. It has been recently shown that NORE, a non-catalytic polypeptide homologous to the putative tumor suppressor RASSF1, associates with Mst1 and the NORE-Mst1 complex mediates Ras-dependent apoptosis in fibroblasts (46). Thus, Mst1 may be involved in a wide variety of extracellular stimuli as well as environmental stresses. In this regard, Mst1 could be an important therapeutic target in many cardiovascular diseases.

Figure 1B:
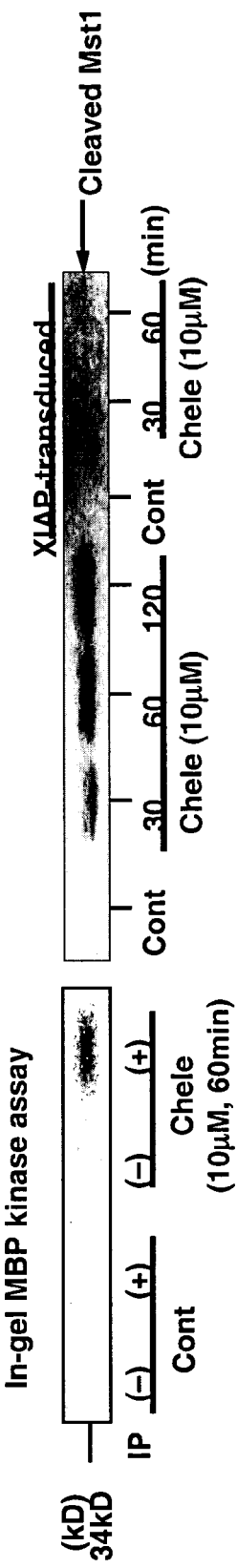
Figure 1C:
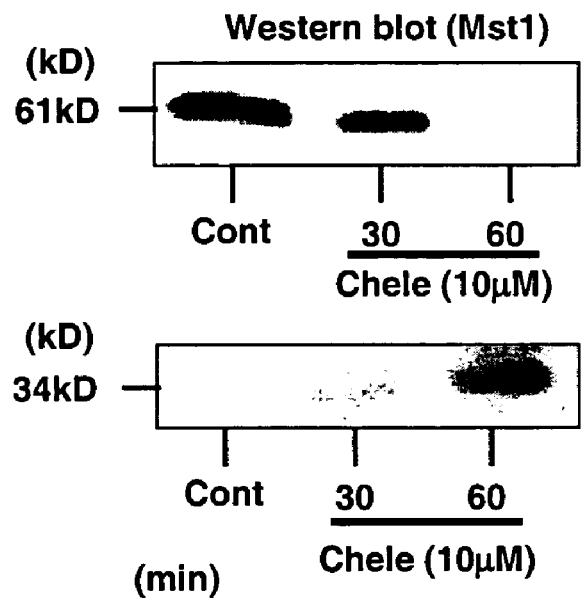
Figure 1D:
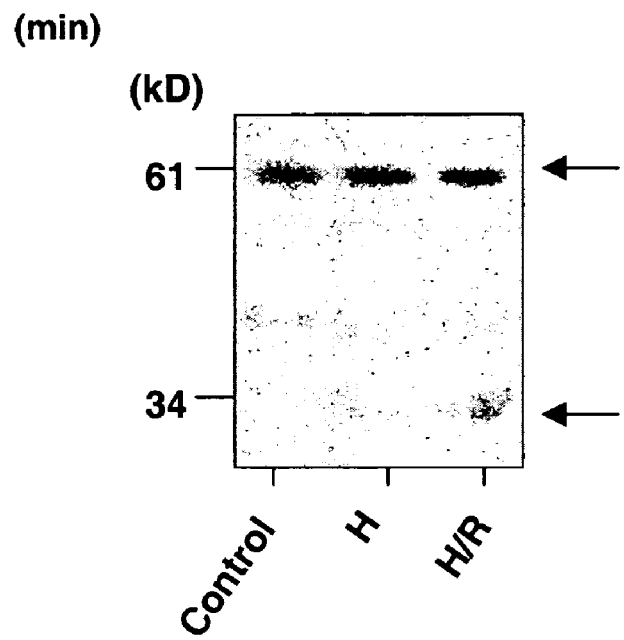

Mst1 is a Predominant MBP Kinase Activated by Potent Stimulators of Apoptosis in Cardiac Myocytes In order to identify the signaling mechanism inducing apoptosis in cardiac myocytes, cardiac myocytes were treated with chelerythrine, a potent inducer of apoptosis (35). The whole cell extracts prepared from chelerythrine-treated myocytes were subjected to in gel kinase assays, using myelin basic protein as a substrate (35). We found that a 34 kD kinase is most prominently activated by chelerythrine at 6–30 μM, the concentrations where apoptosis and activation of caspase-3 are observed (35). Activation of the 34 kD kinase was accompanied by disappearance of a 61 kD kinase (FIG. 1A). Since it has been shown in other cell types that Mst1, a 61 kD kinase, is cleaved by caspases and a resultant 34 kD fragment containing the N-terminal kinase domain becomes active, we examined if the 61 kD and 34 kD proteins are Mst1 in our experiments. Immune complex kinase assays, using specific anti-Mst1 antibody raised against the N-terminal 15 amino acids of Mst1, indicated that the 34 kD form of Mst1 is activated by the chelerythrine treatment (FIG. 1B). Furthermore, immunoblot analyses, using specific anti-Mst1 antibodies, indicated that the 61 kD form of Mst1 is downregulated, while the 34 kD form of Mst1 is concomitantly upregulated after chelerythrine treatment (FIG. 1C), consistent with the changes in activities of the 61 and 34 kD proteins in the in-gel kinase assays. In order to examine if Mst1 is activated by a caspase-dependent cleavage in cardiac myocytes, we transduced cardiac myocytes with XIAP, which we have shown inhibits apoptosis and activation of caspase-3 in cardiac myocytes (35). Activation and cleavage of Mst1 was completely inhibited in the presence of XIAP (FIG. 1B), suggesting that Mst1 is activated by caspase-dependent cleavage in cardiac myocytes. Cleavage and activation of Mst-1 is also induced by hypoxia/reoxygenation, a known stimulus of apoptosis in cardiac myocytes (FIG. 1D).

Figure 1E:
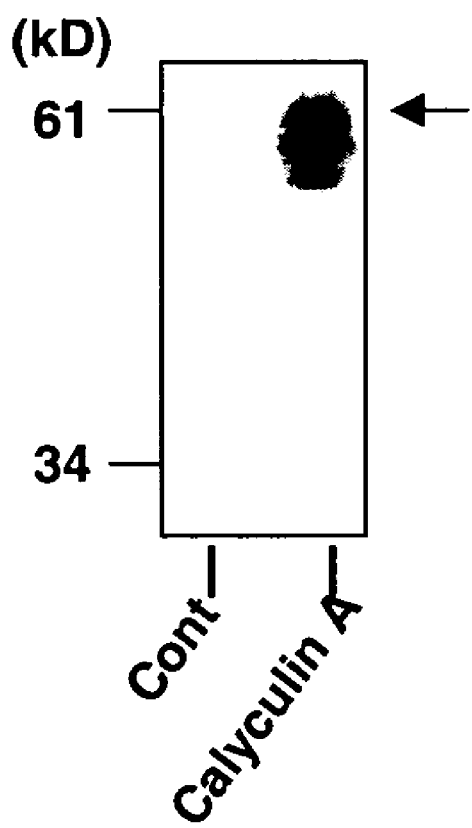

Recent evidence suggests that Mst1 is also activated by phosphorylation of the activation loop even in the absence of cleavage (42). Calyculin A, an inhibitor of protein phosphatase 2A (PP-2A) and PP-1, causes prominent cell death consistent with apoptosis in cardiac myocytes, which is evidenced by significant increases ($4.3\pm1.4$ fold, n=4, p<0.05 vs untreated) in cytoplasmic accumulation of oligo- and mono-nucleosomes. In gel kinase assays indicated that a 61 kD form of Mst1 is strongly activated by calyculin A without activation of the 34 kD form (FIG. 1E). These results suggest that Mst1 is a prominent MBP kinase, which is activated by potent apoptotic stimuli full length (61 kD) forms, is accompanied by prominent cell death in cardiac myocytes.

EXAMPLE 2

Figure 2A:
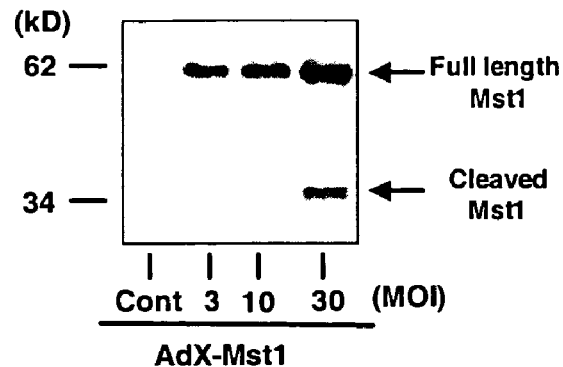
FIGS. 2A, 2B, 2C, 2D, 2E, 2F and 2G. (A to G) Cardiac myocytes were transduced with adenovirus harboring either wild type Mst1 (AdX-Mst1), Mst1 (K59R) (AdX-Mst1 (K59R)) or control adenovirus (Ad5 βgal) at indicated concentrations. Myocytes were harvested 48 h after transduction. Some myocytes (C and F) were treated with a caspase-3 inhibitor (DEVD-CHO, 100 □M). (A and B) Immunoblot analyses were performed by using anti-Mst1 polyclonal antibody. MOI, multiplicity of infection. Cont, control where no virus was applied. (C) In-gel MBP assays were performed. (D) The effect of adenovirus transduction (30 MOI) upon the morphology of cardiac myocytes is shown. Note that cell death with shrinkage is observed in AdX-Mst1 transduced cardiac myocytes. (E and F) Cytoplasmic accumulation of mono- and oligo-nucleosomes, a sensitive indicator of DNA fragmentation by apoptosis, was quantitated by Cell Death ELISA Plus. n=3 (F) (G) Activation caspase-3 was determined by immunoblot analyses with anti-cleaved caspase-3 antibody. n=3.
Figure 2B:
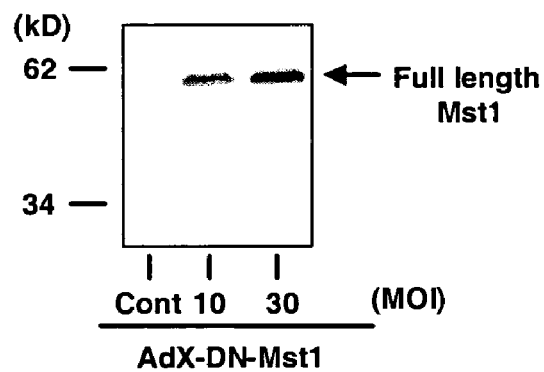
Figure 2C:
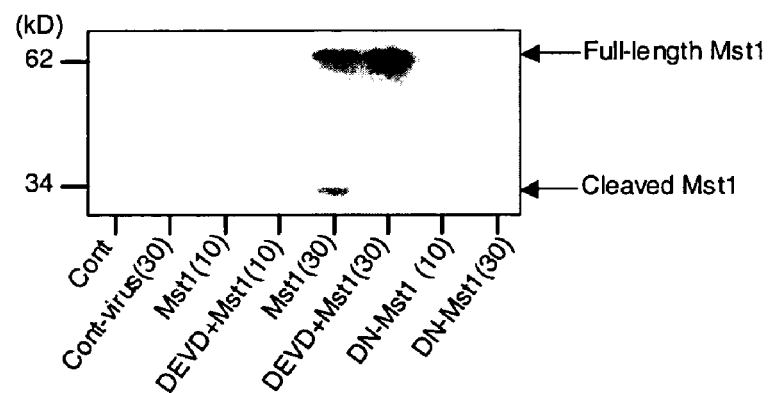
Figure 2D:
Figure 2E:
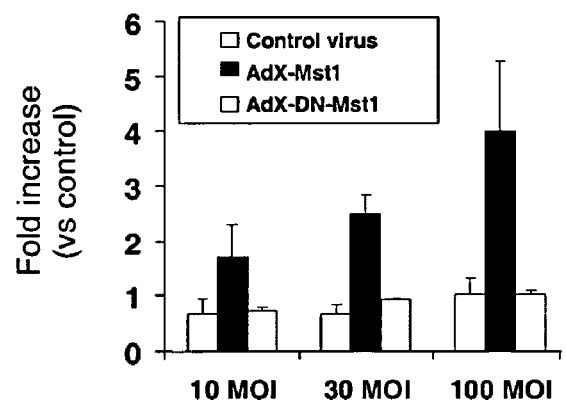
Figure 2F:
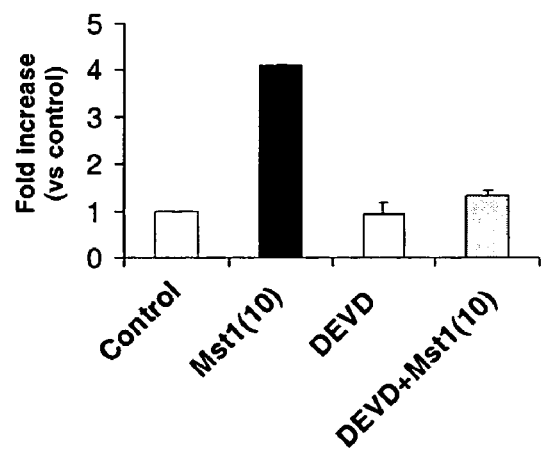
Figure 2G:
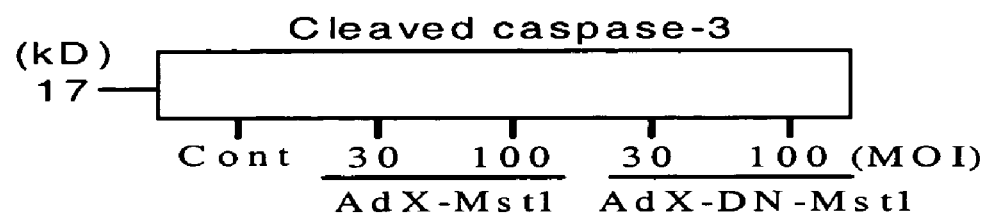

Mst1 Plays an Essential Role in Mediating Apoptosis in Response to Chelerythrine and Calyculin A in Cardiac Myocytes In order to examine if Mst1 promotes apoptosis, we overexpressed either wild type Mst1 or dominant negative Mst1 (Mst1 (K59R)) in cardiac myocytes by using adenovirus transduction. Immunoblot analyses with anti-Mst1 antibody indicated that transduction of adenovirus harboring wild type Mst1 (AdX-Mst1) dose-dependently increased the full length form of Mst1. Expression of the cleaved form of Mst1 was also observed at high doses, suggesting that overexpression of Mst1 alone can induce partial cleavage of Mst1 (FIG. 2A). By contrast, transduction of adenovirus harboring Mst1 (K59R) (AdX-DN-Mst1) increased only the full length form of Mst1 (K59R) (FIG. 2B). In gel kinase assays showed that the MBP kinase activity of Mst1 was significantly increased by overexpression of wild type Mst1, while it was not activated by Mst1 (K59R), confirming that Mst1 (K59R) is kinase inactive (FIG. 2C). Furthermore, increased activities and cleavage of Mst1 by overexpression of Mst1 were attenuated in the presence of a caspase-3 inhibitor, DEVD-CHO, suggesting that Mst1 activates caspase-3, which in turn causes cleavage of Mst1 (FIG. 2C, lane 4). Transduction of either control virus or AdX-DN-Mst1 did not induce any significant changes in the morphology of cardiac myocytes. By contrast, transduction of AdX-Mst1 caused shrinkage and cell death in cardiac myocytes (FIG. 2D). Cytoplasmic accumulation of mono- and oligo-nucleosomes, sensitive indicators of nuclear fragmentation by apoptosis, was dose-dependently increased by overexpression of wild type Mst1 but not by control virus or Mst1 (K59R) (FIG. 2E). Increases in DNA fragmentation by wild type Mst1 were inhibited in the presence of DEVD-CHO (FIG. 2F). Overexpression of wild type Mst1, but not Mst1 (K59R), caused activation of caspase-3, which was determined by immunoblotting with anti-cleaved specific caspase-3 antibody (FIG. 2G). These results suggest that Mst1 induces cardiac myocyte apoptosis in its kinase activity-dependent manner.

Figure 3:
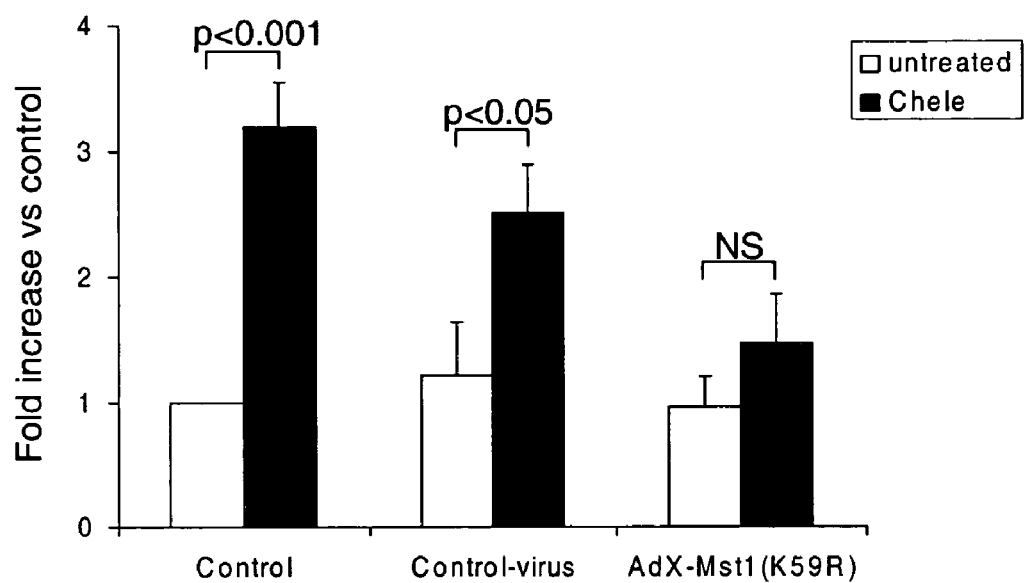
FIG. 3 depicts the effect of dominant negative Mst1 upon chelerythrine-induced cardiac myocyte apoptosis. Cardiac myocytes were transduced with wither control virus or adenovirus harboring dominant negative Mst1 (Mst1 (K59R)). Forty-eight hours after transduction, cardiac myocytes were treated with chelerythrine (10 μM) for 1 h and cytoplasmic accumulation of mono- and oligo-nucleosome was quantitated. n=3.

In order to examine if Mst1 is required for cardiac myocyte apoptosis in response to chelerythrine, cardiac myocytes were transduced with AdX-DN-Mst1 or control virus and challenged by chelerythrine. Cytoplasmic accumulation of mono- and oligo-nucleosome by chelerythrine treatment was significantly suppressed in the presence of AdX-Mst1 (K59R) but not by control virus (FIG. 3). DNA fragmentation by calyculin A was also inhibited by AdX-Mst1 (K59R) (5.6 fold with control virus vs 0.9 fold with AdX-DN-Mst1. These results suggest that both cleaved and full length forms of Mst1 plays a critical role in mediating apoptosis in cardiac myocytes.

EXAMPLE 3

Figure 4:
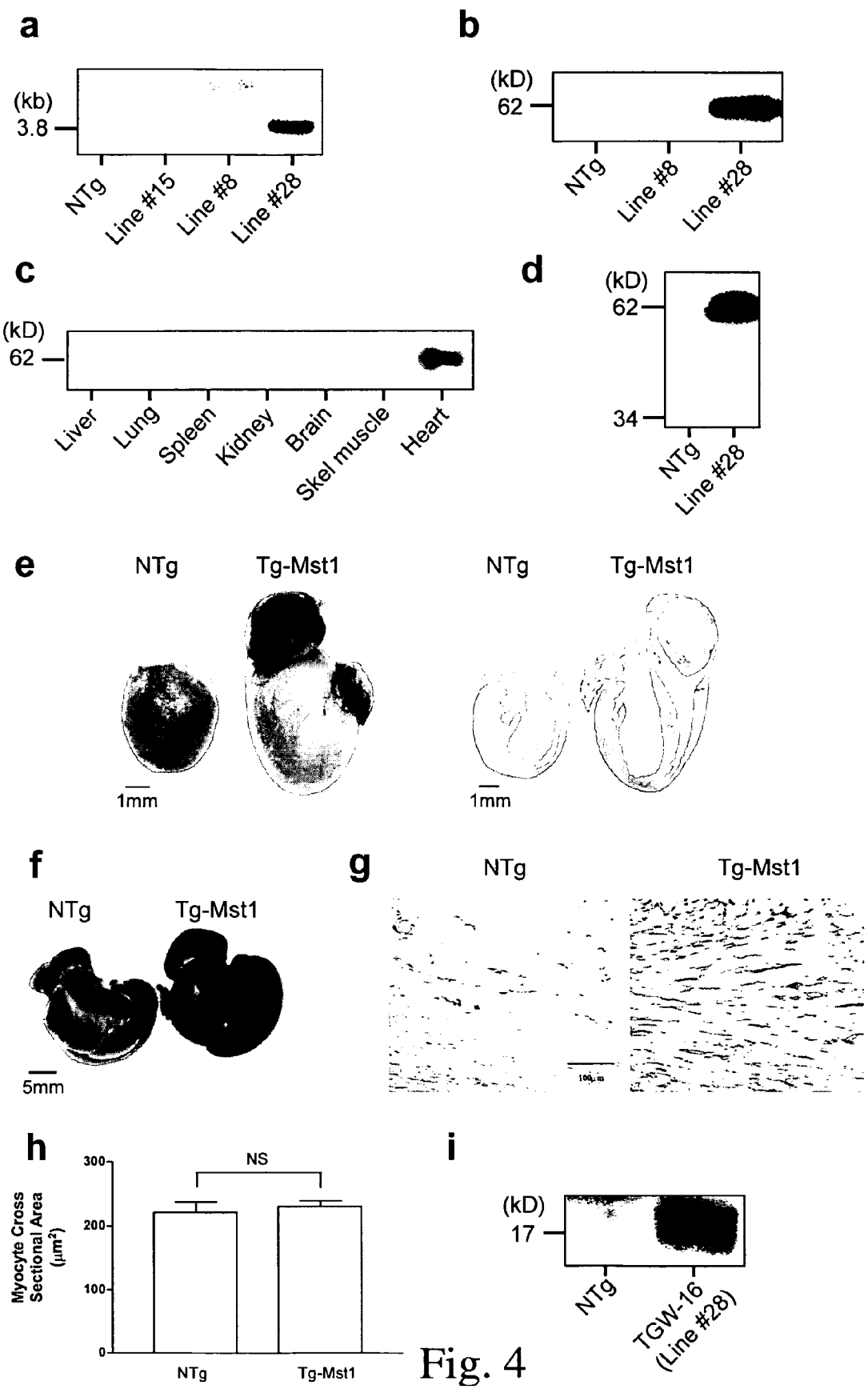
FIGS. 4A, 4B, 4C, 4D, 4E, 4F, 4G, 4H, and 4I. (A) Immunoblot analyses of the heart homogenates with anti-myc antibody. (B) Tissue homogenates were prepared from various organs of Tg-Mst1. Immunoblot analyses were performed with anti-myc antibody. (C) Heart homogenates were prepared from Tg-Mst1 or non-transgenic control mice (Ntg). In-gel MBP kinase assays were performed. (D) Gross appearance and a transverse section of the hearts obtained from Tg-Mst1 and NTg. Hematoxylin Eosin staining was performed (3 months old). (E) A photograph of the liver isolated from Tg-Mst1 and the littermate NTg (3 months old). (F) Picric acid sirius red staining of heart sections obtained from Tg-Mst1 and NTg (1.5 month old). (G) LV cardiac myocyte cross sectional area was obtained from Tg-Mst1 and NTg as described in the Method section. Seven Tg-Mst1 and 4 NTg mice were used for the analysis. (H) Heart homogenates were prepared from Tg-Mst1 and NTg. (I) Immunoblot analyses were performed by using anti-cleaved caspase-3 antibody. n=3.

Cardiac Specific Overexpression of Mst1 in Mice Causes Dilated Cardiomyopathy without Cardiac Myocyte Hypertrophy In order to examine the function of Mst1 in the mouse heart in vivo, transgenic mice with cardiac specific overexpression of wild type (Tg-Mst1) was generated by using the □MHC promoter. We identified three founders with transgene positive by Southern blot analyses. Among them, germ line transmission was observed in two lines. One line (line #28) showed prominent cardiac specific overexpression of wild type Mst1, while the other line (line #8) showed modest overexpression (FIG. 4A). We confirmed that Mst1 is overexpressed predominantly in the heart as expected (FIG. 4B). In-gel MBP kinase assays indicated that the total activity of Mst1 is significantly increased in Tg-Mst1. Increases in the MBP kinase activity in Tg-Mst1 were found predominantly in the full length form rather than in the cleaved form (FIG. 4C).

Interestingly, some Tg-Mst1 exhibited overt signs of heart failure, such as shortness of breath and edema, and died prematurely as early as on Day 15. Echocardiographic measurements of Tg-Mst1 lines #28 and #8 at 70–80 days old indicated that Tg-Mst1 exhibited significant increases in LVEDD and LVESD and significant decreases in LVEF, LV fractional shortening and LV wall thickness (TABLE 1).

TABLE 1

Echocardiographic Analyses of Tg-Mst1

| | Non-transgenic (n = 4) | Tg-Mst1 (n = 5) |
|---|---|---|
| Line #28 (High level overexpression) | | |
| Age (days old) | 75 ± 2.89 | 76 ± 2.45 |
| LVEDD (mm) | 3.92 ± 0.11 | 4.39 ± 0.06* |
| LVESD (mm) | 2.62 ± 0.11 | 3.55 ± 0.10* |
| LVEF (%) | 70.0 ± 1.83 | 47.2 ± 2.80* |
| % FS (%) | 33.1 ± 1.44 | 19.2 ± 1.41* |
| DSEP WT (mm) | 0.59 ± 0.04 | 0.39 ± 0.01* |
| DPW WT (mm) | 0.59 ± 0.02 | 0.37 ± 0.03* |
| HR (bpm) | 246.8 ± 23.4 | 303.0 ± 32.8 |
| *p < 0.01 compared with non-transgenic | | |
| Line #8 (Intermediate level overexpression) | | |
| Age (days old) | 195 ± 1.96 | 193 ± 1.96 |
| LVEDD (mm) | 4.40 ± 0.25 | 4.54 ± 0.28 |
| LVESD (mm) | 2.99 ± 0.14 | 3.29 ± 0.19 |
| LVEF (%) | 68.4 ± 1.21 | 61.6 ± 2.38* |
| % FS (%) | 31.9 ± 0.78 | 27.5 ± 1.46* |
| DSEP WT (mm) | 0.68 ± 0.02 | 0.64 ± 0.03 |
| DPW WT (mm) | 0.65 ± 0.02 | 0.63 ± 0.02 |
| HR (bpm) | 258.2 ± 8.1 | 255.8 ± 25.2 |

*p < 0.05 compared with non-transgenic

Hemodynamic analyses conducted in Tg-Mst1 with (echocardiographically determined) reduced LVEF confirmed that LVEDP was significantly elevated, while LV dP/dt was decreased compared with non-transgenic littermates (TABLE 2).

TABLE 2

Hemodynamic Measurements of Tg-Mst1

|  | Non-transgenic (n = 4) | Tg-Mst1 (n = 5) |
|---|---|---|
| Age (days) | 80 ± 7.8 | 88 ± 12 |
| LVSP (mmHg) | 84 ± 2.3 | 70 ± 5.1 |
| LVEDP (mmHg) | 3.3 ± 2.9 | 18.6 ± 1.5** |
| +LV dP/dt | 5200 ± 245 | 4300 ± 663 |
| −LV dP/dt | 4467 ± 356 | 3080 ± 481 |
| RVSP (mmHg) | 18 ± 2.9 | 29 ± 3.3* |
| RVEDP (mmHg) | 0.7 ± 0.4 | 9.0 ± 2.2* |
| RAP (mmHg) | 1.3 ± 0.4 | 7.0 ± 2.3 |
| HR (bpm) | 323 ± 54 | 297 ± 36 |

*$p < 0.05$,
**$p < 0.001$ compared with non-transgenic

Necropsy of Tg-Mst1 performed at 1–2 months indicated dilation of all 4 cardiac chambers, mural thrombus formation with occasional fibrous structures in both atriums, and reduced wall thickness, consistent with the findings of dilated cardiomyopathy (TABLE 3 and FIG. 4D). Although LA and RA weight/body weight of Tg-Mst1 was significantly higher than that of non-transgenic littermate, LV weight/body weight and RV weight/body weight were not significantly different between Tg-Mst1 and non-transgenic littermate (TABLE 3). Significant increases in lung weight/body weight and liver weight/body weight and visible congestion of the liver were observed in Tg-Mst1 compared with non-transgenic littermate (TABLE 3 and FIG. 4E). The lungs were congested (FIG. 4F). Histological analyses of the heart sections indicated that TUNEL positive myocytes are significantly increased in Tg-Mst1 (control 0.06±0.03%, Tg-Mst1 0.30±0.05%, n=4, p<0.01). The level of interstitial fibrosis significantly increased in all four chambers of Tg-Mst1 (FIG. 4G). These results suggest that myocyte death and subsequent replacement of myocardium with fibrous tissue took place in Tg-Mst1 hearts. Interestingly, the cross sectional areas of cardiac myocytes in the LV was not significantly different between Tg-Mst1 and non-transgenic mice confirming that there was no compensatory cardiac myocyte hypertrophy in Tg-Mst1 (FIG. 4H). The level of cleaved caspase-3 was increased in hearts of Tg-Mst1 (FIG. 4I). Although it was smaller in extent, reduced cardiac function and increased levels of cardiac myocyte apoptosis were also found in line #8 of Tg-Mst1.

TABLE 3

Postmortem Pathologic Measurements of Tg-Mst1

|  | Non-transgenic (n = 9) | Tg-Mst1 (n = 12) |
|---|---|---|
| Age (days) | 46.7 ± 2.7 | 46.9 ± 1.9 |
| Body weight (g) | 18.4 ± 0.4 | 19.4 ± 0.8 |
| LV (mg) | 64.2 ± 2.0 | 64.5 ± 2.6 |
| RV (mg) | 19.1 ± 0.8 | 20.6 ± 0.6 |
| LV/body weight | 3.48 ± 0.07 | 3.32 ± 0.06 |
| Lung/body weight | 6.67 ± 0.30 | 7.73 ± 0.29* |
| Liver/body weight | 47.6 ± 1.78 | 55.1 ± 2.71* |

*$p < 0.05$ compared with non-transgenic
**$p < 0.01$ compared with non-transgenic

EXAMPLE 4

Figure 5:
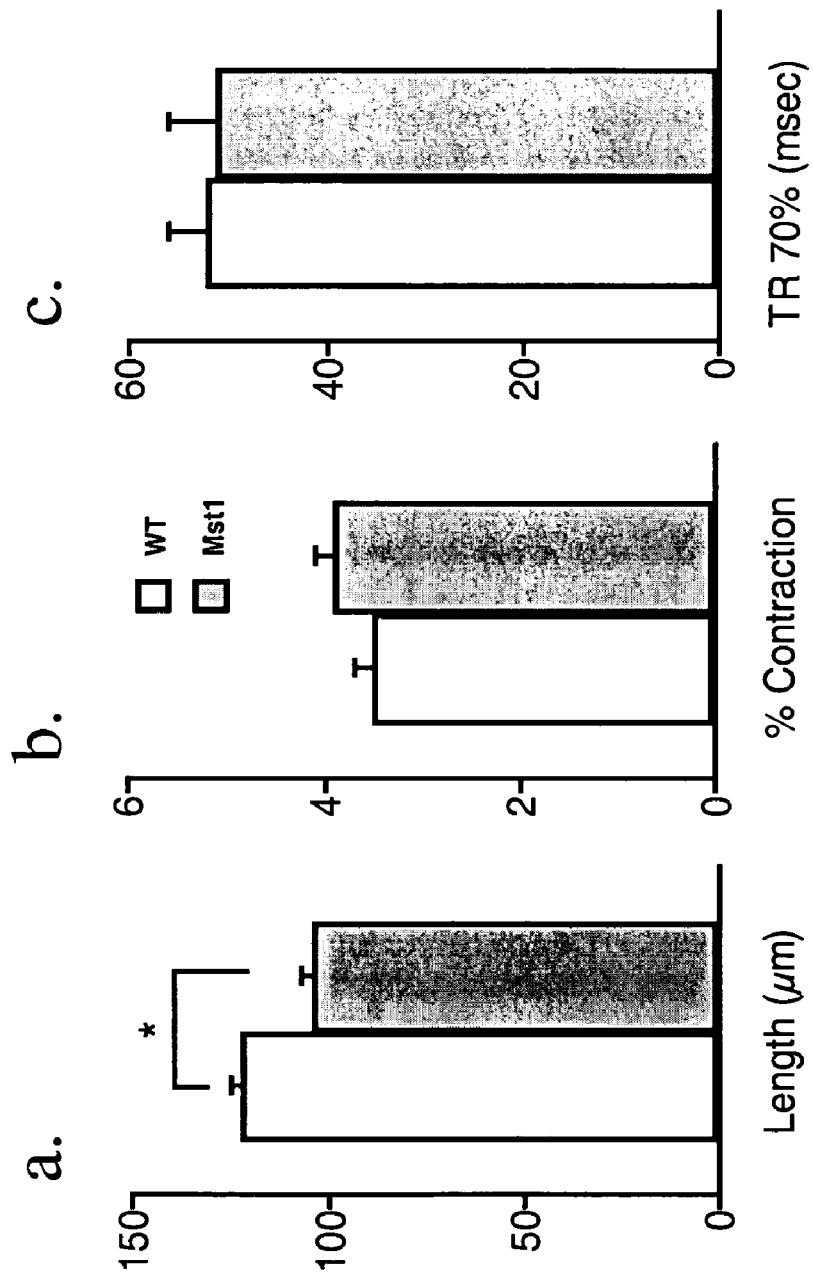
FIG. 5 depicts myocyte length and contractile (% contraction) and relaxation (TR 70%: time for 70% relengthening) function. Myocyte length was significantly reduced, p<0.05, in myocytes from Tg-Mst1 (n=4, 111 cells) compared with WT (n=4, 129 cells). There was no change in contractile and relaxation function.

Contractile Function of Individual Cardiac Myocytes Isolated from Tg-Mst1 is Not Altered In order to examine the mechanism of reduced cardiac function in Tg-Mst1, cardiac myocytes were isolated from 3 months old Tg-Mst1 and non-transgenic control mice and their contractile properties were evaluated by using the edge detection method. Echo cardiographic measurements indicated that LVEF of the Tg-Mst1 mice used in these experiments was significantly lower than that of non-transgenic mice (Tg-Mst1 51±5% vs non-transgenic littermate 68±1%, p<0.05, n=4). There were no significant differences in % contraction and the rate of relaxation of isolated cardiac myocytes between Tg-Mst1 and non-transgenic mice (FIG. 5), suggesting that the decreases in cardiac contractility in Tg-Mst1 may not be primarily caused by decreases in the contractile or relaxation function of individual cardiac myocytes. Interestingly, the length of ventricular myocytes isolated from Tg-Mst1 was smaller than those from non-transgenic controls.

EXAMPLE 5

Expression of Nuclear Encoded Cytochrome C Oxidase is Reduced in Tg-Mst1

Figure 8A:
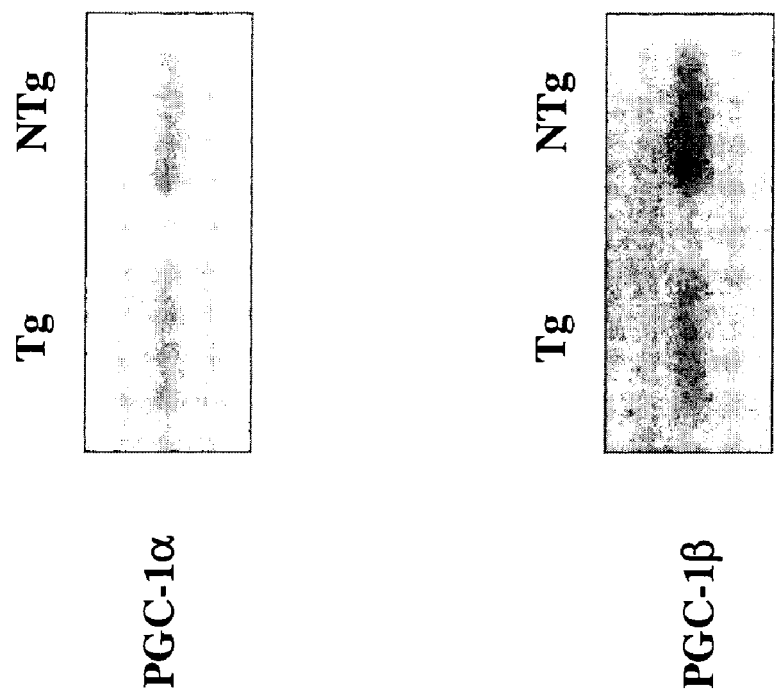
FIGS. 8A and 8B depicts mRNA expression of PGC-1α and β is downregulated in Tg-Mst1 (PGC-1 is a nuclear transcription co-factor, which plays an important role in regulating expression of nuclear encoded mitochondrial genes). RT-PCR results are shown. Each band in the gel shown in (A) represents RNA combined from 2 separate hearts. Mice were approximately 2 months old. Data represents a single experiment. The relative RNA levels are graphed in (B).
Figure 8B:
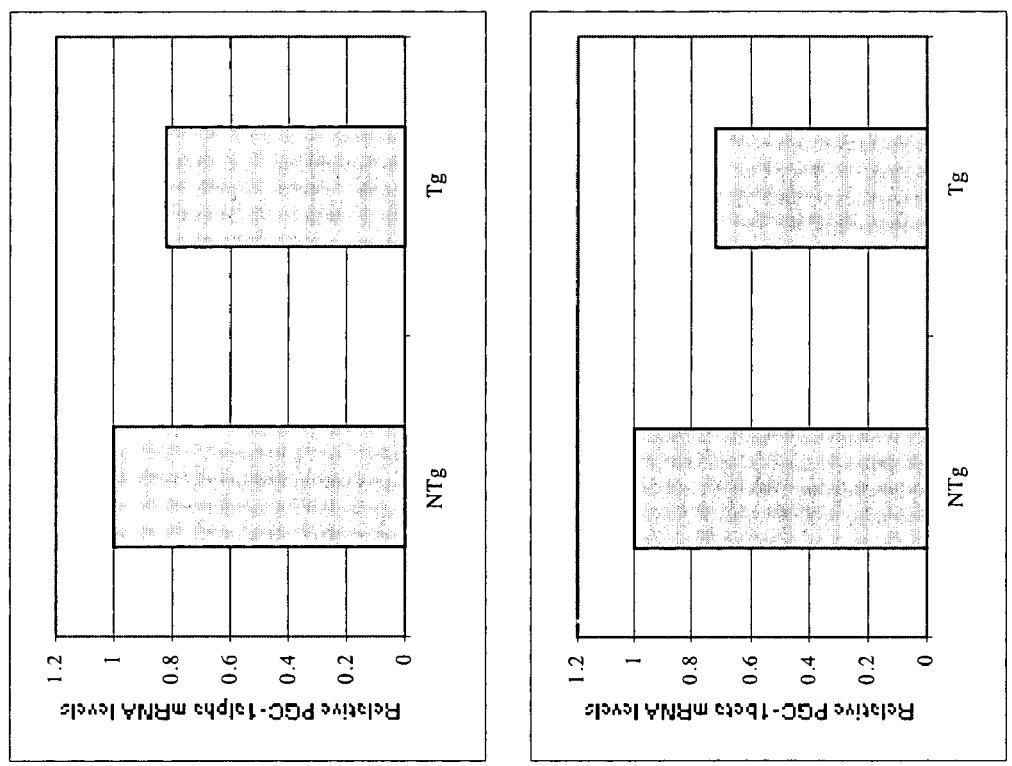
Figure 9A:
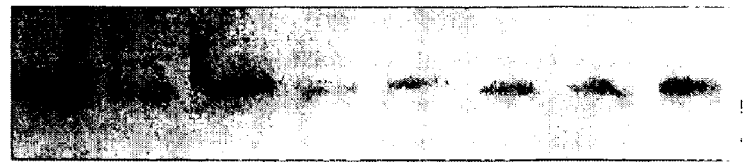
FIGS. 9A and 9B depicts that protein expression of cytochrome c oxidase is downregulated in Tg-Mst1 animals. Western blots of protein from nontransgenic (N) and transgenic (T) individual animals are shown in (A) for cytochrome c oxidase VIIa (COX VIIa), IV (COX IV) and Vb (COX Vb). Relative protein expression for each COX is graphed in (B). Data are mean+SEM.
Figure 9A:
Figure 9A:
Figure 9B:
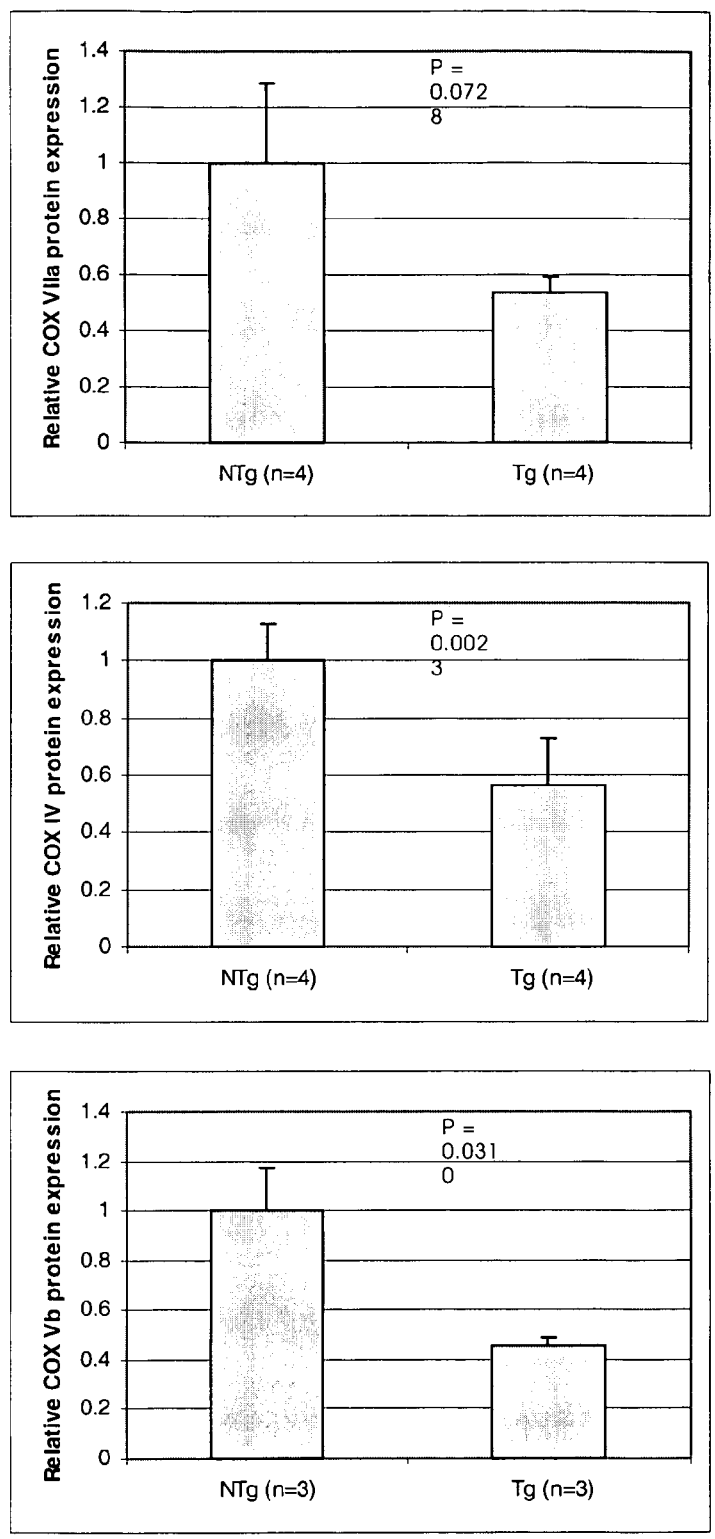

In order to examine the mechanism of dilated cardiomyopathy in Tg-Mst1, we performed DNA microarray analyses. PolyA RNA was isolated from the hearts of Tg-Mst1 and non-transgenic littermate at the age of 2 months, those who did not show overt signs of congestive heart failure. The list of the genes, whose expression was consistently upregulated or downregulated in three independent analyses, is shown in TABLE 4. Classification of the identified genes according to their function indicates that many genes regulating both mitochondrial and cytoplasmic metabolism are downregulated in Tg-Mst1. Among them, we found that some components of nuclear encoded cytochrome c oxidase subunits are consistently downregulated by 21–64%. Exemplary RT-PCR results are shown in FIG. 8 which demonstrates that mRNA expression of PGC-1α and PGC-1β are each decreased in transgenic Tg-Mst1 mice. PGC-1 is a nuclear transcription co-factor which plays an important role in regulating expression of nuclear encoded mitochondrial genes. Proteomic analysis, although more limited in scope, showed similar results. In particular and exemplary of the protein analysis, FIG. 9 shows Western blots and tabulated expression of Cytochrome C oxidase complex proteins COX VIIa, COX IV and COX Vb in transgenic versus non-transgenic animals.

TABLE 4

Genes constantly upregulated or downregulated in Tg-Mst1 in three independent microarray analyses

|  | mean % change | SEM |
|---|---|---|
| Upregulated genes | | |
| matrix gamma carboxylglutamate protein | 584 | 270 |
| procollagen 1 alpha 1 subunit | 702 | 457 |
| peptidylprolyl isomerase A | 77 | 12 |
| natriuretic peptide precursor type B | 819 | 278 |

TABLE 4-continued

Genes constantly upregulated or downregulated in Tg-Mst1 in three independent microarray analyses

|  | mean % change | SEM |
|---|---|---|
| desmin | 199 | 95 |
| Downregulated genes | | |
| Mitochondrial metabolism | | |
| COX7A1 | −74 | 15 |
| COX7C | −59 | 11 |
| COX4 | −47 | 20 |
| COX5B | −55 | 12 |
| COX8B | −54 | 18 |
| ATPase inhibitor | −12 | 4 |
| mitochondrial malate dehydrogenase | −53 | 10 |
| soluble malate dehydrogenase | −43 | 14 |
| NADH dehydrogenase flavoprotein 1 | −52 | 2 |
| NADH-ubiquinone oxidoreductase MWFE subunit | −54 | 24 |
| Cytoplasmic metabolism | | |
| gamma neuronal enolase 2 | −62 | 8 |
| muscle creatine kinase | −72 | 4 |
| lactate dehydrogenase 2B subunit | −40 | 8 |
| soluble superoxide dismutase 1 | −28 | 4 |
| prosaposin | −85 | 10 |
| Others | | |
| vascular endothelial growth factor B | −47 | 8 |
| cardiac troponin I | −59 | 11 |
| Ia-associated invariant chain | −64 | 25 |

EXAMPLE 6

Figure 6A:
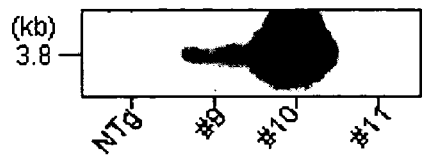
FIGS. 6A, 6B, 6C, 6D, 6E and 6F depicts analyses of Tg-DN-Mst1 or non-transgenic control (nTg) mice. In (A) three transgenic lines, #9, #10 and #11, are probed for Mst1 expression in the heart. In (B) Immunoblot analyses of the heart homogenates with anti-myc antibody. In (C)–(F). Tg-DN-Mst1 or non-transgenic control mice (NTg) were subjected to 20 mm ischemia and 24 h reperfusion or sham operation. (C) The heart homogenates (100 μg) obtained from ischemic (I) and non-ischemic (N) areas of the left ventricle (LV) or from intact LV of the sham operated mice were subjected to in gel myelin basic protein (MBP) kinase assays. Ischemia/reperfusion (I/R) increased kinase activities of Mst1 in the ischemic area of NTg mice, while activation of Mst1 by I/R was completely abolished in Tg-DN-Mst1. (D) The effect of I/R upon the extent of LV myocardial infarction (MI) in Tg-DN-Mst1 and NTg control mice. The MI area/area at risk (AAR) was determined as described in the Method section. Note that MI area/AAR was significantly smaller in Tg-DN-Mst1 compared with that in NTg. (E) LV tissue sections were subjected to TUNEL staining and DAPI staining. n=11. (F) Genomic DNA was isolated from non-ischemic (N) and ischemic (I) areas and DNA laddering assays were performed. The extent of DNA laddering in response to I/R was significantly smaller in Tg-DN-Mst1 compared with that in NTg. n=3.
Figure 6B:
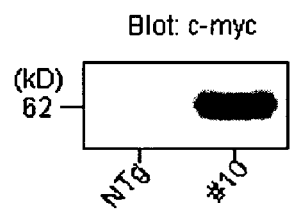
Figure 6C:
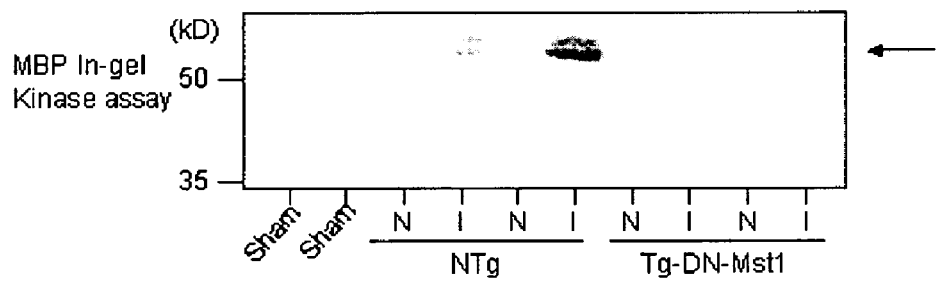
Figure 6D:
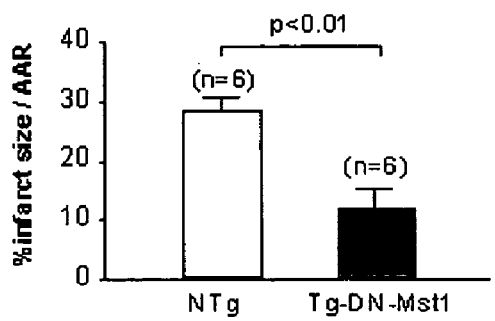
Figure 6E:
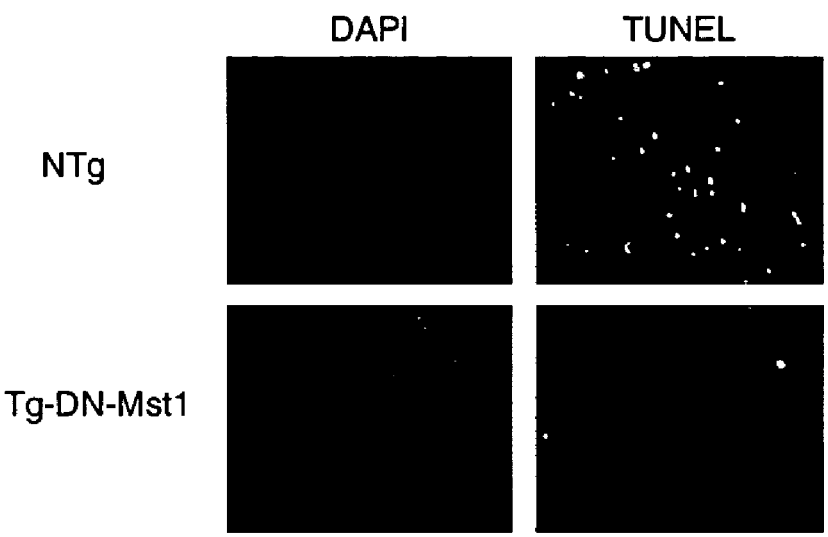
Figure 6F:
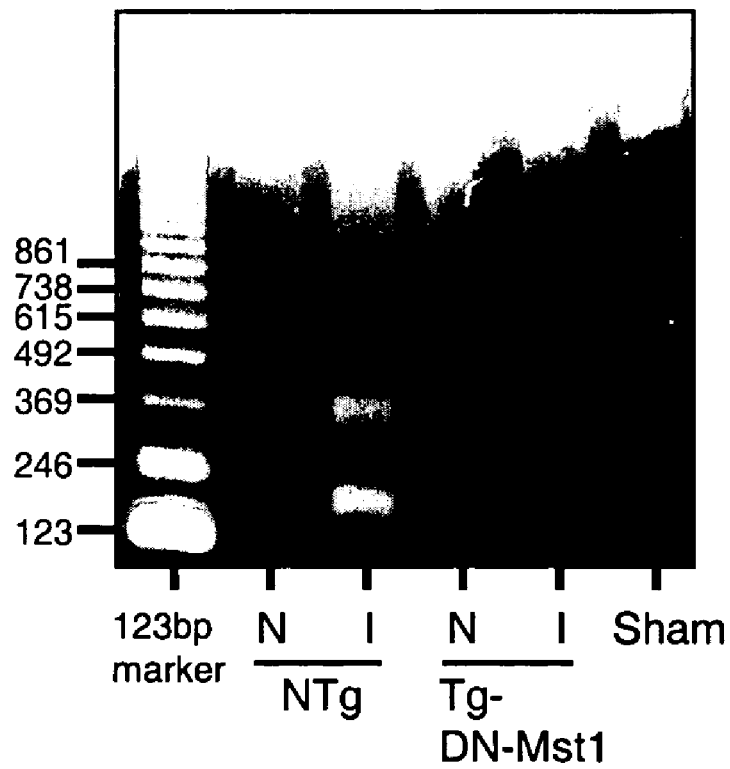

Cardiac Specific Overexpression of Mst1 (K59R) Works as Dominant Negative Mst1 and Significantly Reduces Myocardial Infarction and Apoptosis in Response to I/R In order to examine if Mst1 plays a critical role in mediating apoptosis in response to pathologic insults to the hearts, we generated transgenic mice with cardiac specific overexpression of dominant negative Mst1 (Mst1 (K59R)) (Tg-DN-Mst1). Among three lines generated, line #10 expressed the highest level of Mst1 (K59R) in the heart (FIG. 6A). Tg-DN-Mst1 did not show premature death or any signs of heart failure. The results of echocardiographic measurements of Tg-DN-Mst1 were not significantly different from those of non-transgenic littermates (TABLE 5). These results suggest that development of dilated cardiomyopathy in Tg-Mst1 is dependent upon the kinase activity of Mst1. In order to examine if overexpression of Mst1 (K59R) works as dominant negative, we applied 20 min of ischemia and subsequent 24 h of reperfusion into the mouse heart. Results of the in gel MBP kinase assays showed that I/R activates Mst1 primarily in the full length form in the control mouse hearts (FIG. 6B). By contrast, activities of Mst1 at basal conditions as well as in response to I/R were abolished in Tg-DN-Mst1, suggesting that cardiac specific overexpression of Mst1 (K59R) works as dominant negative for endogenous Mst1 (FIG. 6C). The extent of myocardial infarction in response to I/R, quantitated by the TTC staining of the area at risk, was significantly smaller in Tg-DN-Mst1 compared with that in non-transgenic littermate. The heart section obtained from the ischemic area of Tg-DN-Mst1 exhibited a smaller number of TUNEL positive myocytes compared with that of non-transgenic littermate (FIG. 6D). Electrophoresis of genomic DNA prepared from the ischemic area of non-transgenic mice exhibited a typical pattern of DNA laddering. By contrast, DNA laddering was significantly suppressed in Tg-DN-Mst1 (FIG. 6E). These results suggest that inhibition of Mst1 reduces both cardiac myocyte apoptosis and the size of myocardial infarction in mouse hearts.

TABLE 5

Echocardiographic Analyses of Tg-DN-Mst1

|  | NTg (n = 9) | TG-DN-Mst1 (n = 8) |
|---|---|---|
| Age (days) | 92 ± 5.5 | 102 ± 4.7 |
| BW (g) | 23 ± 0.6 | 22 ± 1.0 |
| DSWT (mm) | 0.6 ± 0.03 | 0.6 ± 0.02 |
| LVDD (mm) | 3.6 ± 0.11 | 3.9 ± 0.08 |
| DPWT (mm) | 0.6 ± 0.03 | 0.6 ± 0.03 |
| LVSD (mm) | 88 ± 6 | 87 ± 5 |
| % EF (%) | 68 ± 1.2 | 70 ± 0.9 |
| % FS (%) | 32 ± 0.9 | 33 ± 0.6 |
| HR (bpm) | 271 ± 16 | 231 ± 26 |

EXAMPLE 7

Figure 7A:
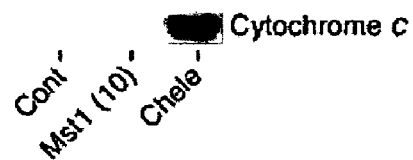
FIGS. 7A, 7B, 7C and 7D depicts (A) Cardiac myocytes were transduced with either control virus (Cont) or AdX-Mst1 (Mst1) at 10 MOI for 48 h. As positive control, myocytes were treated with chelerythrine (Chele, 10 µM) for 1 h. The mitochondria-free cytosolic fraction was obtained. Western blot analysis was performed using anti-cytochrome c antibody (Pharmingen, San Diego, Calif.). Cytochrome c oxidase IV immunoreactivity was negligible in these samples. Chele caused a release of cytochrome c to the cytosolic fraction. Expression of Mst1 increased release of cytochrome c. n=3. (B,C) Cardiac myocytes were transduced with either control virus or AdX-Mst1 (Mst1) at indicated MOIs for 48 h. (upper) Immunoblot analyses were conducted using anti-phospho p38-MAPK antibody (B) or anti-phospho JNK antibody (C). (lower) The filters were re-probed with anti-p38-MAPK antibody (B) or anti-JNK1 antibody (C). In b and c, Similar results were obtained in 4 experiments. (D) Cardiac myocytes were transduced with either control virus or AdX-DN-Mst1 virus. Myocytes were then stimulated with or without chelerythrine (Chele, 10 µM) for 60 min. Myocyte lysates were subjected to immunoblot analysis using anti-phospho p38-MAPK antibody. The filter was re-probed with anti-p38-MAPK antibody. Similar results were obtained in 3 experiments.
Figure 7B:
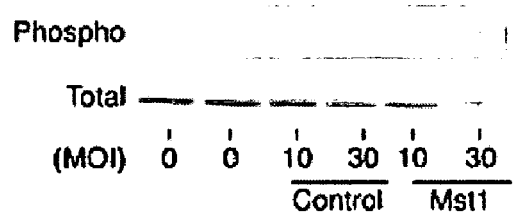
Figure 7C:
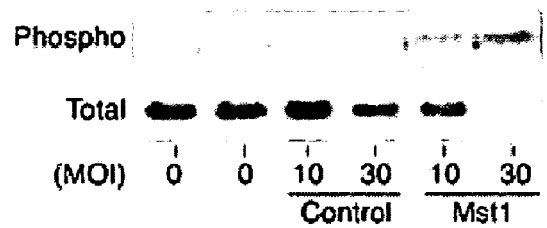
Figure 7D:
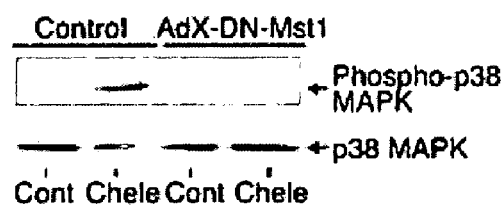

We further examined the mechanism by which Mst1 stimulates apoptosis in cardiac myocytes. Transduction of Mst1 (Tg-Mst1) significantly (two fold, n=3, P<0.05) increased the amount of cytochrome c in the mitochondria-free cytosolic fraction compared with that of control virus, suggesting that release of cytochrome c may contribute to the proapoptotic effect of Mst1 (FIG. 7A). Transduction of Mst1 modestly activated p38-MAPK and p46-JNKs (FIGS. 7B and 7C), while that of the dominant negative Mst1 (Tg-DN-Mst1) abolished chelerythrine-induced activation of p38-MAPK in cardiac myocytes (FIG. 7D). These results suggest that Mst1 works as MAP4K in cardiac myocytes and that it plays an important role in mediating activation of p38-MAPK by chelerythrine.

EXAMPLE 8

Mst1 Directly Inhibits Cardiac Hypertrophy

We have previously and above shown that mammalian sterile-20 like kinase 1 (Mst1) plays an important role in mediating cardiac myocyte apoptosis in response to ischemia/reperfusion and doxorubicin treatment. Cardiac specific overexpression of Mst1 in transgenic mice (Tg-Mst1) increases cardiac myocyte apoptosis in the heart and the mice develop dilated cardiomyopathy (DCM) and congestive heart failure within 3 months of age. Surprisingly, histological analyses of the left ventricular (LV) cardiac myocyte cross sectional area and measurements of the longitudinal length of isolated ventricular cardiac myocytes indicated that there was no compensatory cardiac myocyte hypertrophy in Tg-Mst1 and that myocytes are actually shorter despite elevated wall stress caused by DCM. Lack of compensatory cardiac myocyte hypertrophy may adversely affect LV function of Tg-Mst1 because operation of the Frank Starling mechanism could be less efficient at the individual cell level. This study was undertaken in order to elucidate if transient expression of Mst1 has a direct anti-hypertrophic effects in cultured cardiac myocytes in vitro. Neonatal rat cardiac myocytes were transduced with adenoviral vectors (10 MOI) in serum-free conditions for 48 h and then treated with phenylephrine (PE, 10 μM) for 48 h. Phenylephrine stimulates hypertrophy of cardiac myocytes in normal animals. Treatment of LacZ virus-transduced myocytes with PE caused a 2.4 fold increase in the cell size and a 1.7 fold increase in protein/DNA content. By contrast, transduction of adenovirus harboring Mst1 completely inhibited PE-induced increases in cell size and protein/DNA content. Mst1 also inhibited PE-induced increases in mRNA expression of atrial natriuretic factor by 49%. Interestingly, Mst1 inhibited PE-induced (10 min treatment) activation of ERK by 28%. In summary, Mst1 has a direct anti-hypertrophic effect upon PE-treated cultured cardiac myocytes, possibly affecting other signaling mechanisms, including ERKs. Our results suggest that the proapoptotic signaling mechanism can directly affect hypertrophic signaling mechanisms, thereby contributing to the pathogenesis of cardiomyopathy.

EXAMPLE 9

Figure 10:
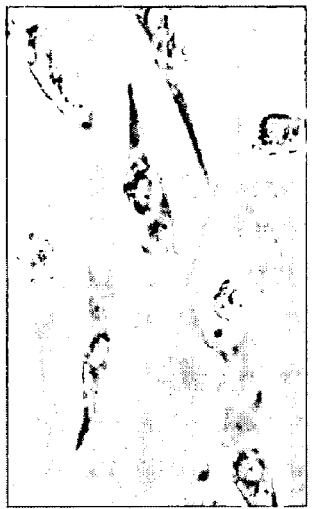
FIG. 10 depicts neonatal rat cardiac myocytes after 6 hour stimulation with Doxorubicin (Doxo). Control myocytes show no evidence of shrinkage, vacuolization, or pyknosis. After 6 hours of Doxo induction, myocytes show a dose dependent cell shrinkage and nuclear pyknosis.
Figure 10:
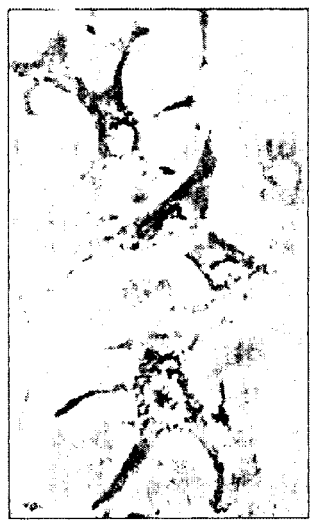
Figure 10:
Figure 11:
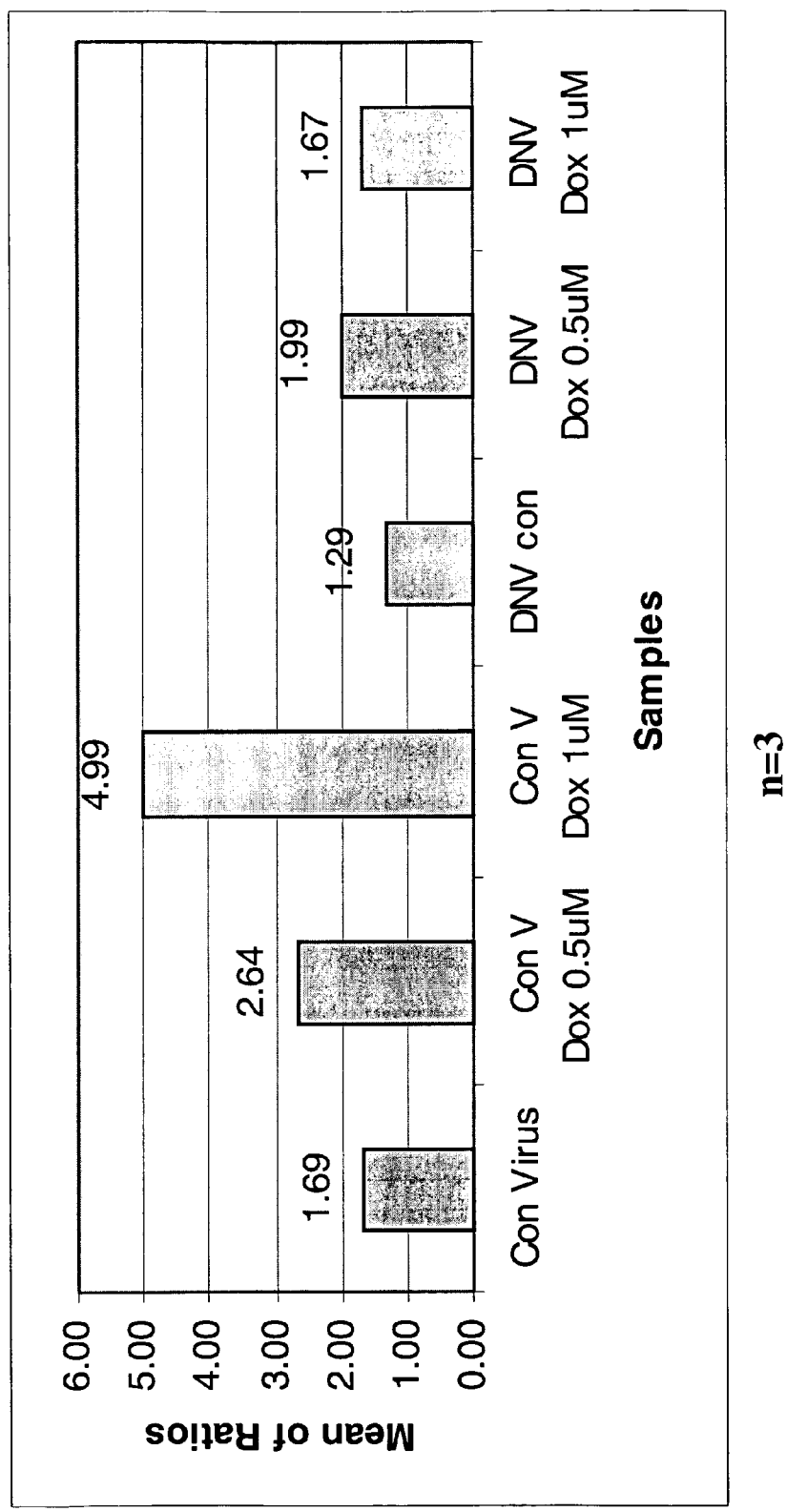
FIG. 11 ELISA shows a reduction of mono- and oligo-nucleosome content in the Adx-Dn-Mst1 treated group after 6 hrs of Doxo stimulation. OD 405, 5 moi of control virus (Lac Z) and DN-Mst1 virus (DNV) respectively. Most likely the slight decrease in the DNV Doxo 1 mM lane is due to increased necrosis of cells in the wells at this dose.
Figure 12:
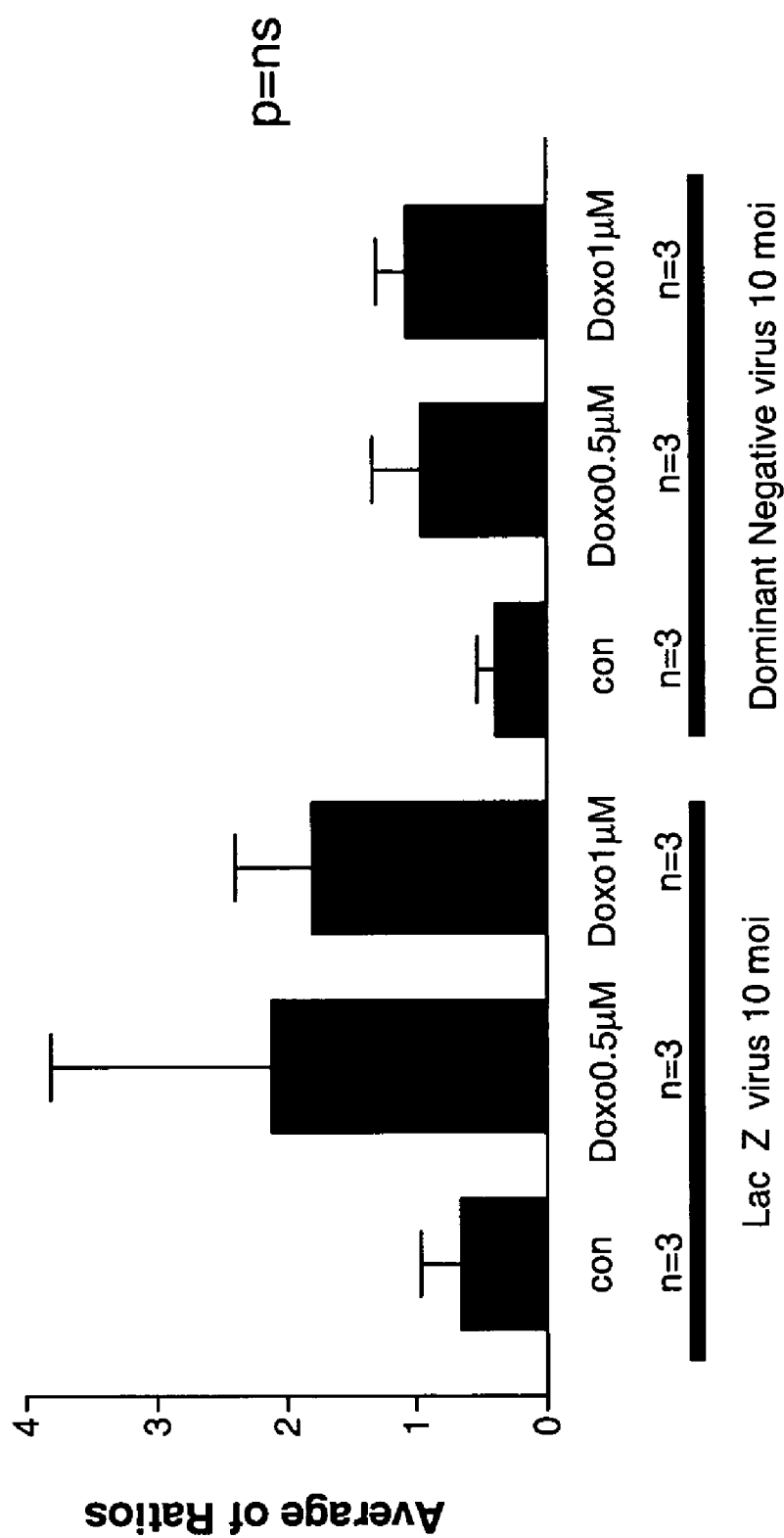
FIG. 12 depicts a cell death ELISA which again shows a trend in the reduction of mono- and oligo-nucleosome content in the Adx-Dn-Mst1 treated group after 6 hrs of Doxo stimulation. OD 405 with 10 moi of Lac Z and DN-Mst1 AdX respectively.
Figure 13:
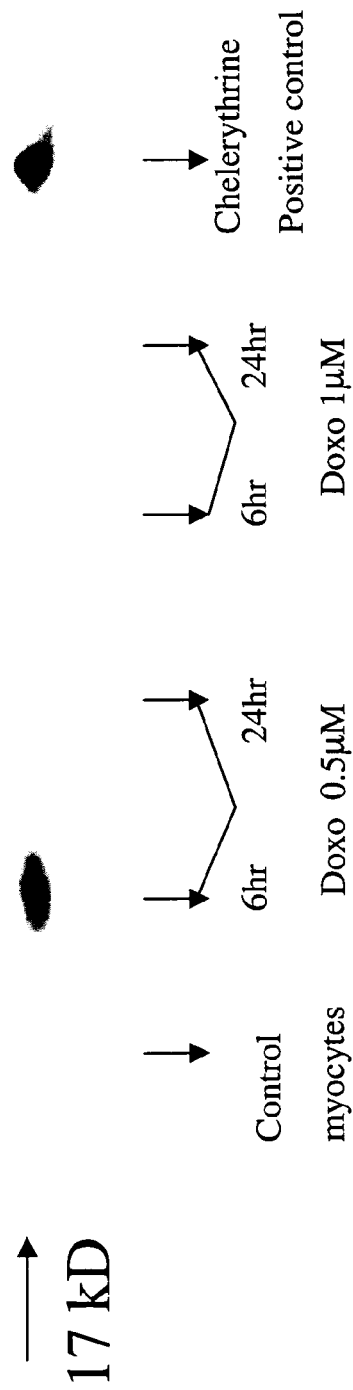
FIG. 13 provides a Western blot depicting cleavage of caspase-3 in the presence of Doxo at the 6 and 24 hour time points. Data suggest that Doxo treatment activates caspase-3 in a time dependent manner.
Figure 14:
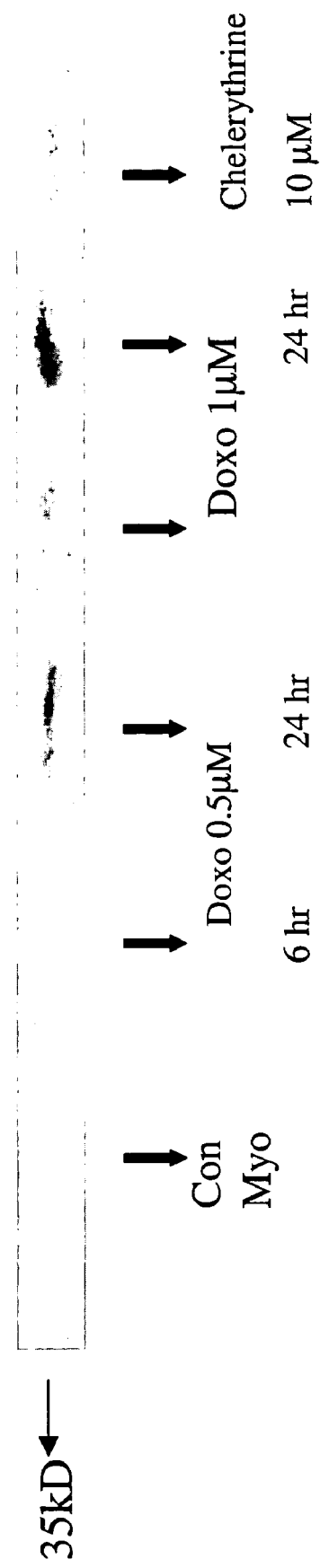
FIG. 14 shows a stripped membrane of the previous (FIG. 13) CC-3 antibody reprobed with CC-9 antibody. This western blot also depicts cleavage of caspase-9 in the presence of Doxo at the 6 and 24 hour time points, with the stronger band appearing at the 24 hour time point. Data suggest that Doxo treatment activates caspase-9 in a time dependent manner.
Figure 15:
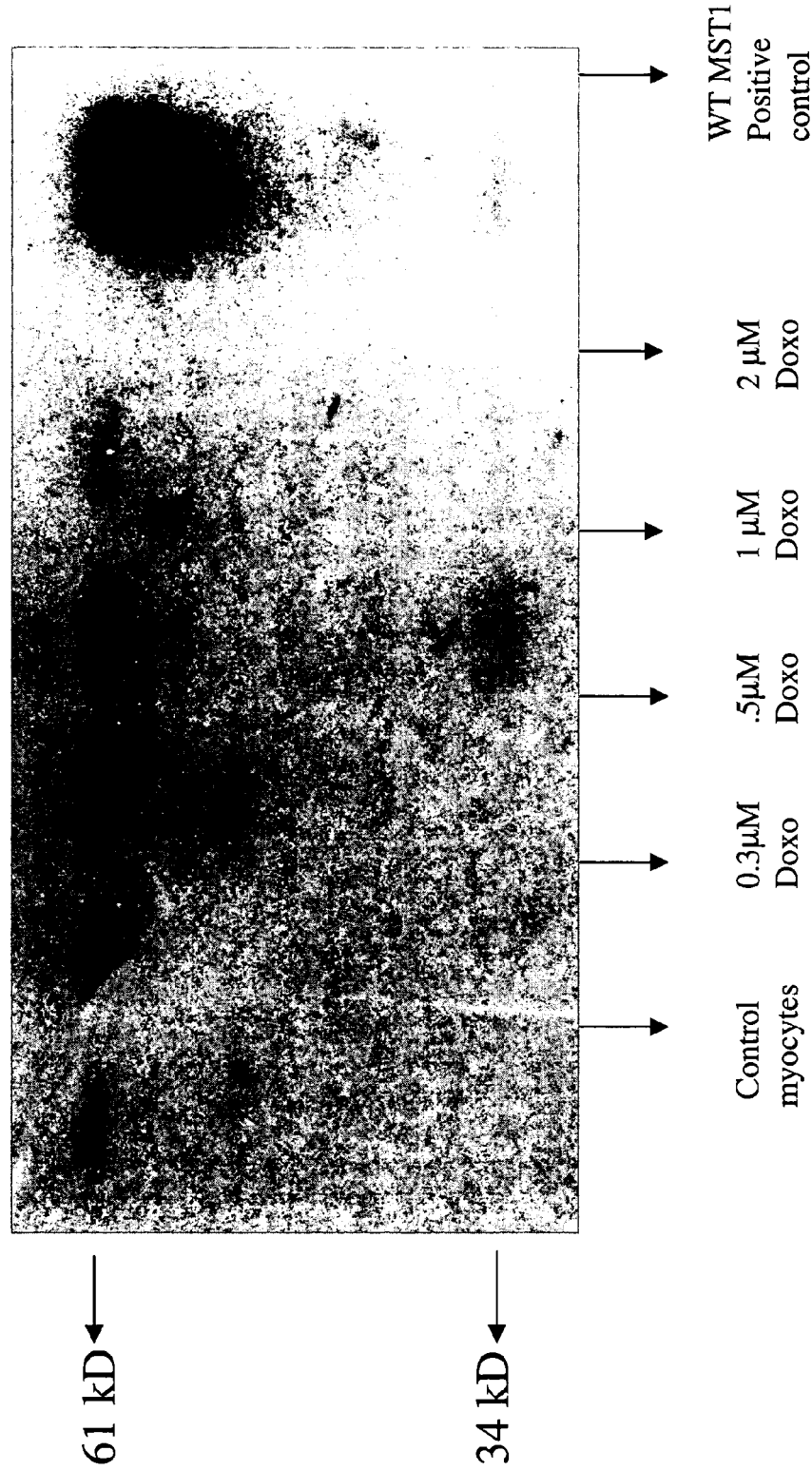
FIG. 15 provides an in gel kinase assay depicting activation of the full length (61 kD) and cleaved (34 kD) forms of Mst1 after 6 hr Doxo stimulation of cardiac myocytes. Myelin basic protein is a major substrate that binds Mst1 during phosphorylation.
Figure 16:
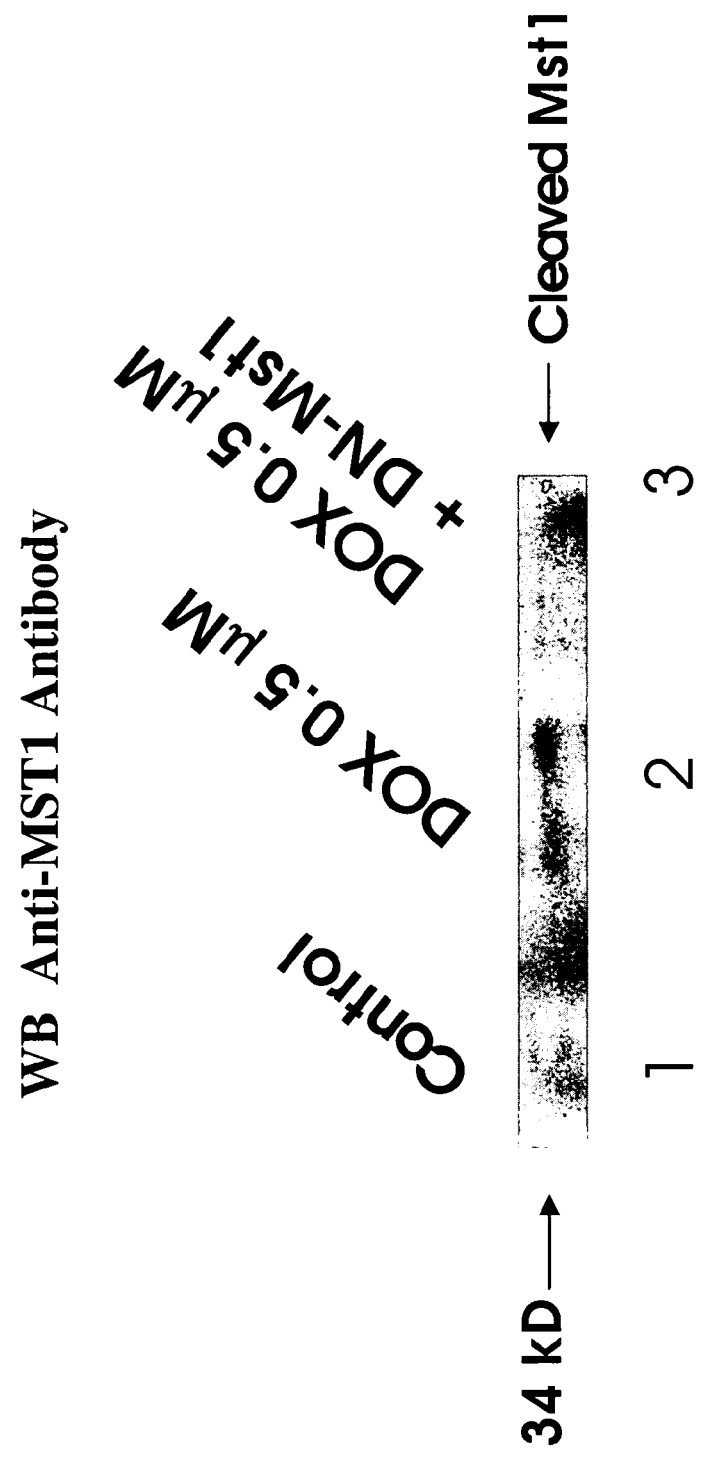
FIG. 16 depicts a Western blot with MST1 antibody after 6 hrs of stimulation of neonatal cardiac myocyte culture with Doxo, showing cleaved Mst-1 at the 0.5 mM dose. Doxo activates cleaved Mst1 but in the presence of DN-Mst1 this reaction is suppressed.
Figure 17:
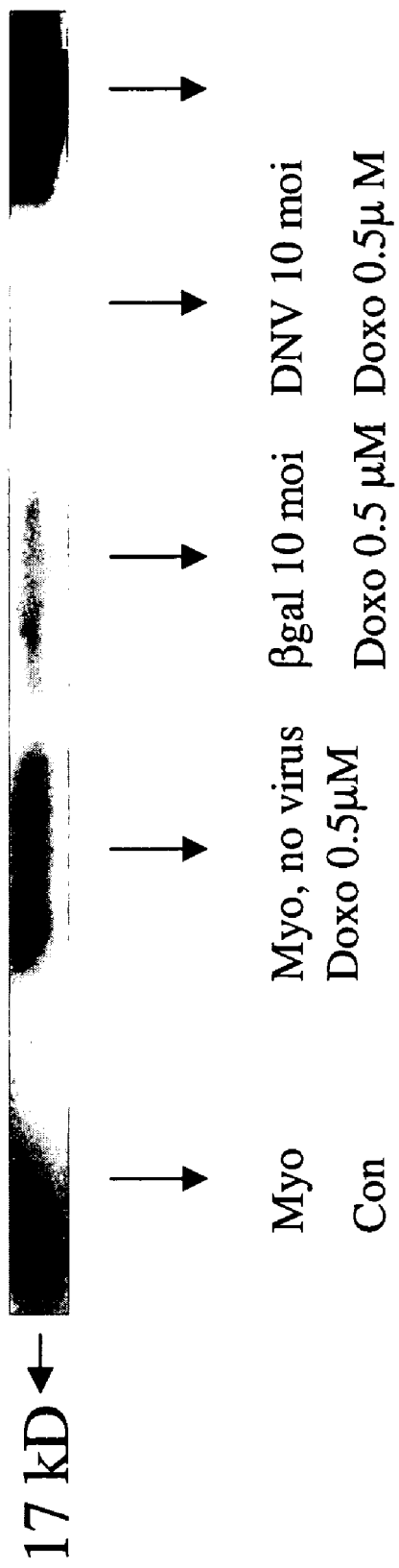
FIG. 17 depicts an immunoblot of cardiac myocytes exposed to 10 moi of either βgal (Lac Z) or DN-Mst1 adenovirus prior to all myocytes being exposed to 6 hr. of Doxo stimulation. In the presence of the DN virus, there is no activation of cleaved caspase –3 when compared to βgal and uninfected myocytes stimulated with Doxo 0.5 mM.
Figure 18:
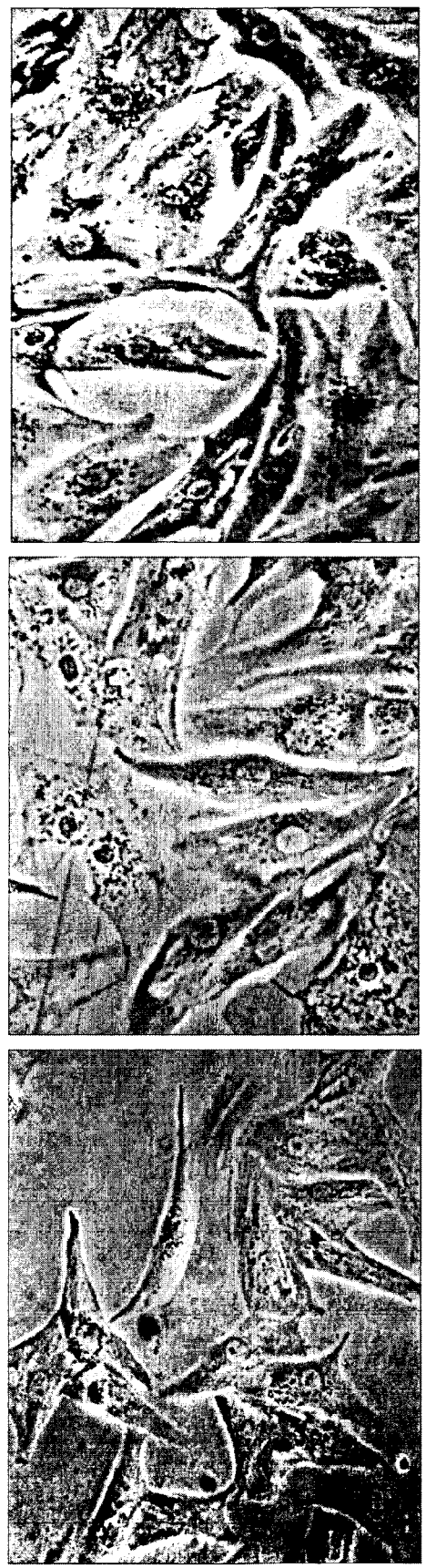
FIG. 18 compares 10 moi control virus (βgal) and 10 moi Adx-DN-Mst1 at baseline and after 6 hrs of stimulation with Doxo. Cell death and shrinkage are noted in the control virus specimen treated with Doxo but not in the Adx-DN-Mst1 treated specimen. This suggests that DN-Mst1 inhibits cardiac myocyte apoptosis by Doxo.
Figure 19:
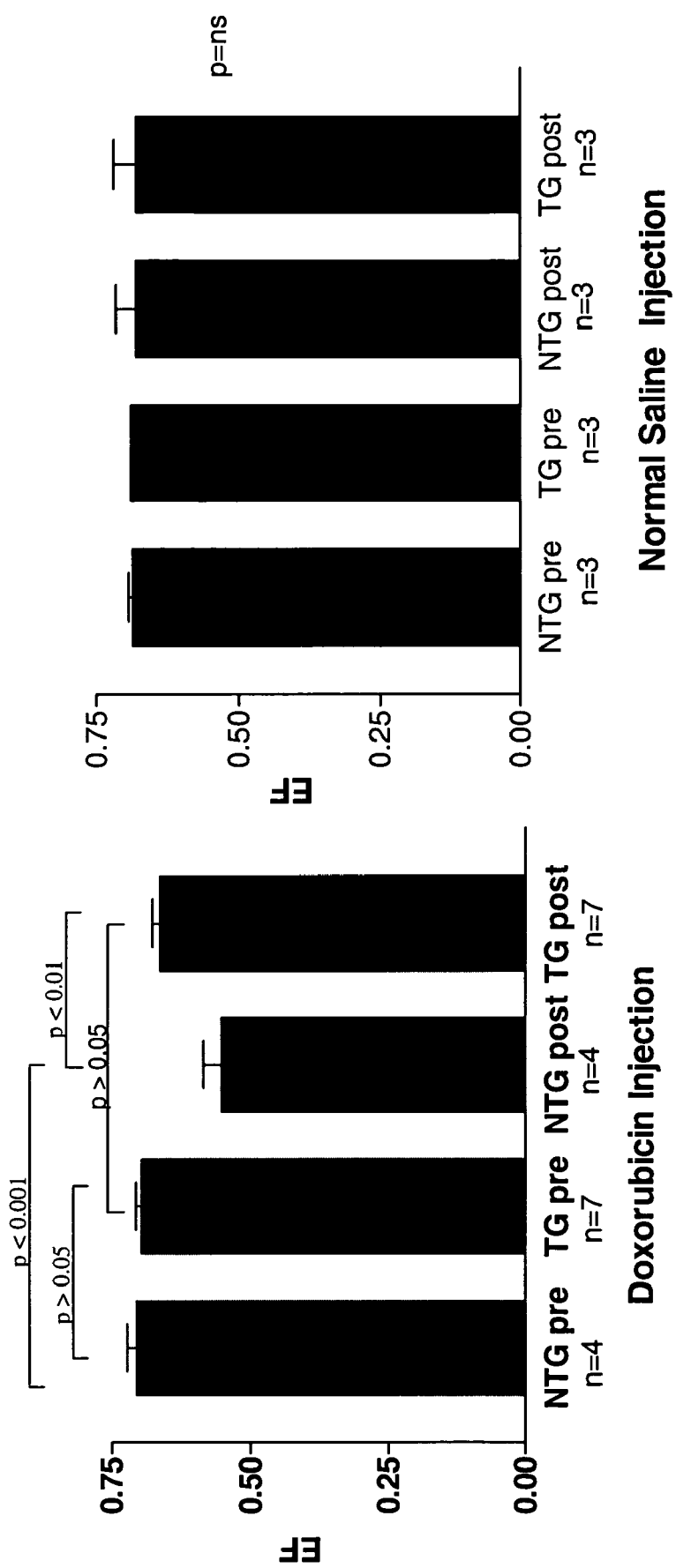
FIG. 19 compares control and dominant negative transgenic mice with and without Doxo injection. Dominant negative transgenic mice receiving the Doxo injection maintain ejection fraction post Doxo injection when compared to their non-transgenic litermates. This suggests that Dn-Mst1 confers a protective effect, possibly inhibiting apoptosis so contractility is maintained.
Figure 20:
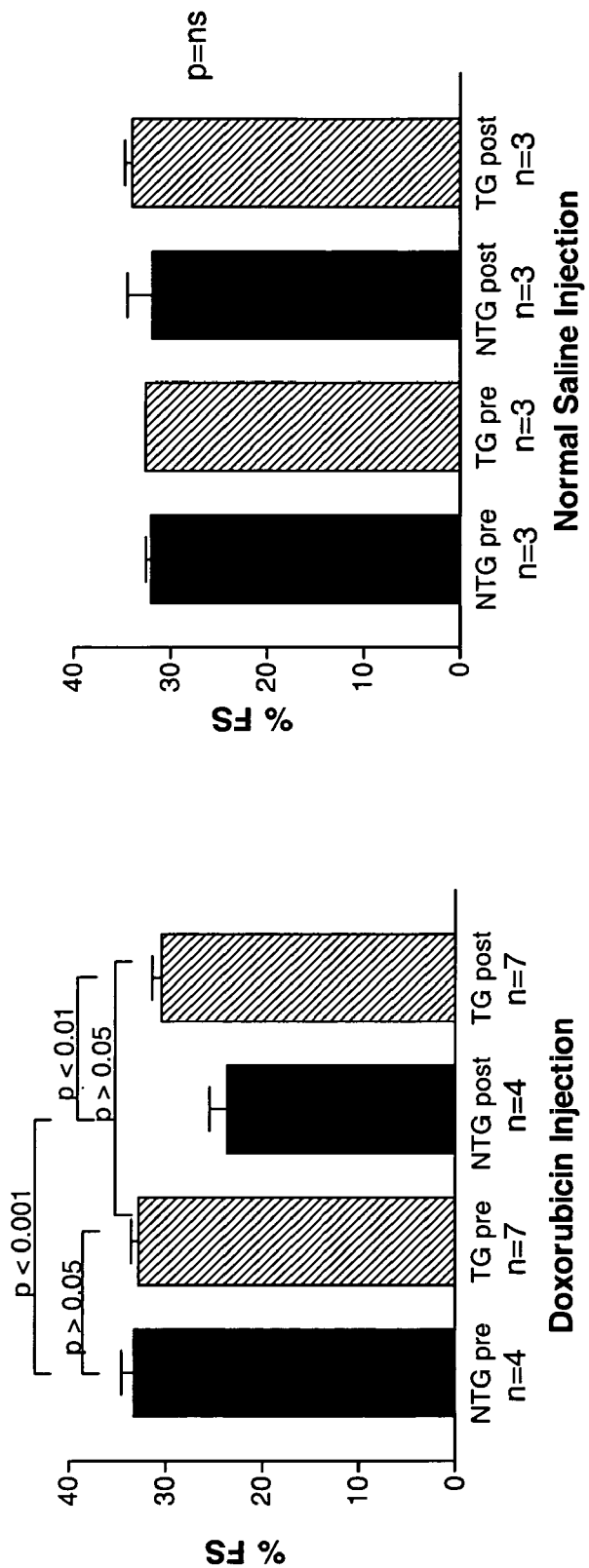
FIG. 20 compares control and dominant negative transgenic mice with and without Doxo injection. Dominant negative transgenic mice receiving the Doxo injection maintain their % fractional shortening post Doxo injection when compared to their non-transgenic litermates. This suggests that Dn-Mst1 confers a protective effect, possibly by inhibiting apoptosis to maintain contractility.
Figure 21:
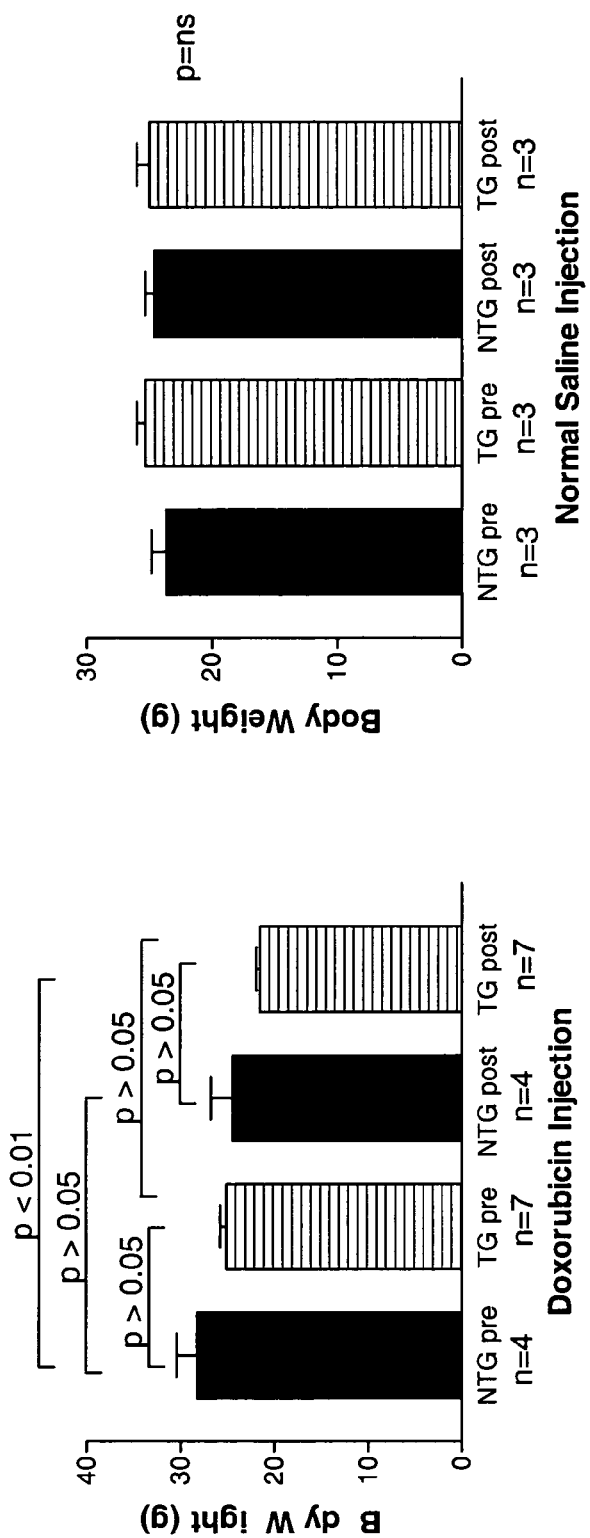
FIG. 21 compares the body weights of the non-transgenic an DN-Mst1 mice pre and post injections of Doxo and normal saline. The significant loss of weight between the NTG pre and DN-TG post Doxo injection mice is most likely due to the well known side effect of anorexia that accompanies Doxo treatment.
Figure 22:
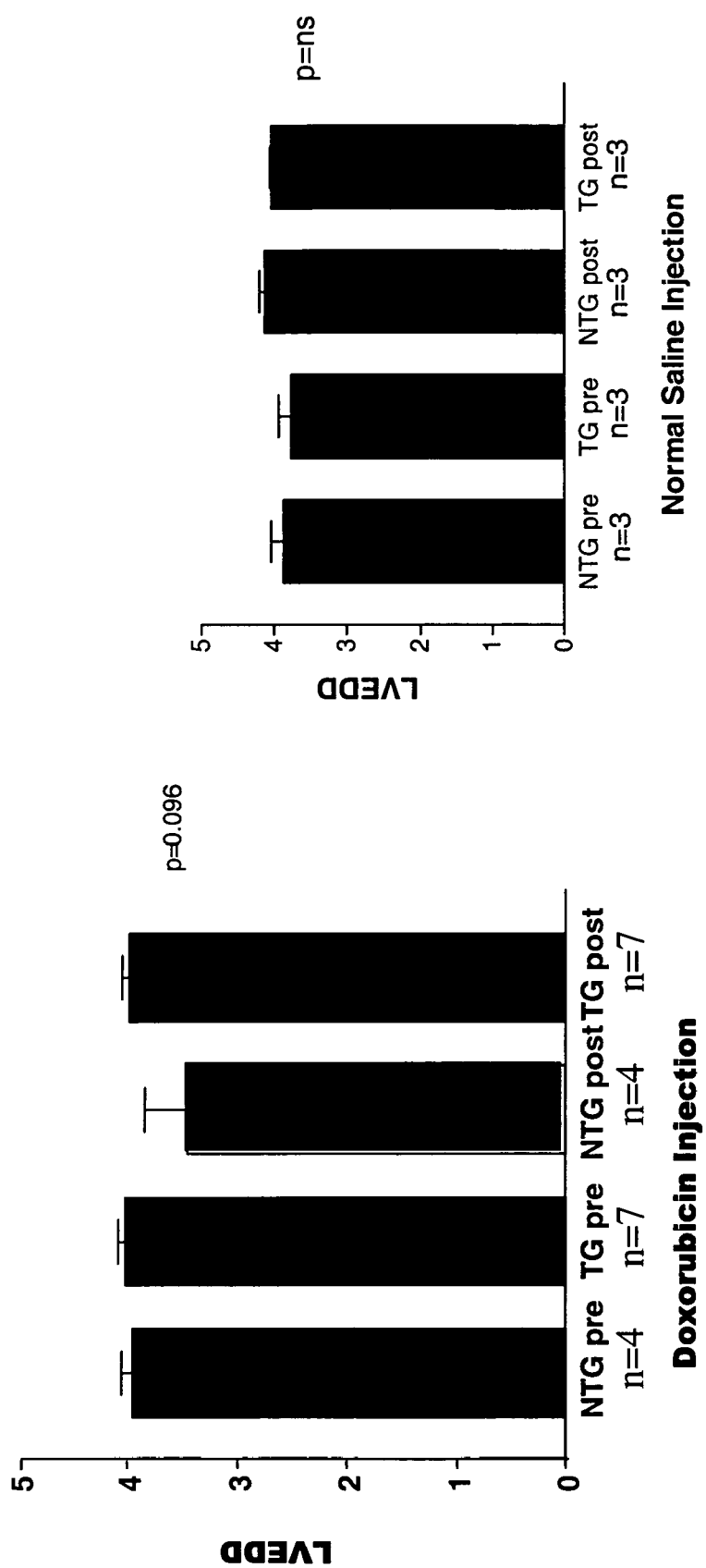
FIG. 22 compares the LVEDD of the non-transgenic and DN-Mst1 mice pre and post Doxo/normal saline treatment. The p value is not significant.

Mst1 Plays an Essential Role in Mediating Cardiac Myocyte Apoptosis by Doxorubicin and Doxorubicin-Induced Cardio-Toxicity Mst1 is an ubiquitously expressed serine-threonine kinase, which is activated by caspase-mediated cleavage and promotes apoptosis in many cell types, including cardiac myocytes. Doxorubicin (Dox or Doxo) belongs to the anthracycline class of anticancer drugs. The limiting factor in the clinical use of Dox is the fact that it induces dose-dependent and irreversible cardiomyopathy. Recent evidence suggests that Dox induces cardiac myocyte apoptosis, which may contribute to the cardiotoxicity of this compound. However, the signaling mechanism of cardiac myocyte apoptosis by Dox is not well understood. We hypothesized that Mst1 mediates cardiac myocyte apoptosis by Dox. In order to address this issue, we used neonatal rat cardiac myocyte cultures and adenovirus transduction. Treatment of cardiac myocytes with Dox (0.1–3 µM) dose-dependently induced cell shrinkage within 6 h (FIG. 10), which was accompanied by activation of caspase-3 and DNA fragmentation, which was determined by cytoplasmic accumulation of mono- and oligo-nucleosome (FIGS. 11 and 12). These results suggest that Dox induces apoptosis in cardiac myocytes. Immunoblot analyses indicated that Mst1 is cleaved to form a 34 kD fragment after 6 h treatment with Dox at 0.1–3 µM (FIG. 16). Immunoblot analysis also demonstrated cleavage of caspase-3 and caspase-9, to activate these enzymes in a time dependent manner on treatment with Dox (FIGS. 13 and 14). In-gel kinase assays, using myelin basic protein as a substrate, showed that cleavage of Mst1 is accompanied by activation of Mst1 (FIG. 15). Interestingly, adenovirus-mediated transduction of dominant negative Mst1 significantly reduced cell shrinkage and DNA fragmentation by Dox treatment, while that of control virus showed no effects (OD405 values after 6 h treatment with 0.5 µM Dox: control virus 0.69 vs dominant negative Mst1 virus 0.21) (FIG. 18). Dominant negative Mst1 mice receiving Dox maintain ejection fraction and % functional shortening when compared to their non-transgenic littermates (FIGS. 19 and 20). In summary, Mst1 is activated by Dox in cardiac myocytes. Mst1 plays an important role in mediating Dox-induced cardiac myocyte apoptosis. Mst1 may be an important therapeutic target of Dox-induced cardiomyopathy.

EXAMPLE 10

Mst1 Plays a Critical Role in Cardiac Remodeling

Figure 23A:
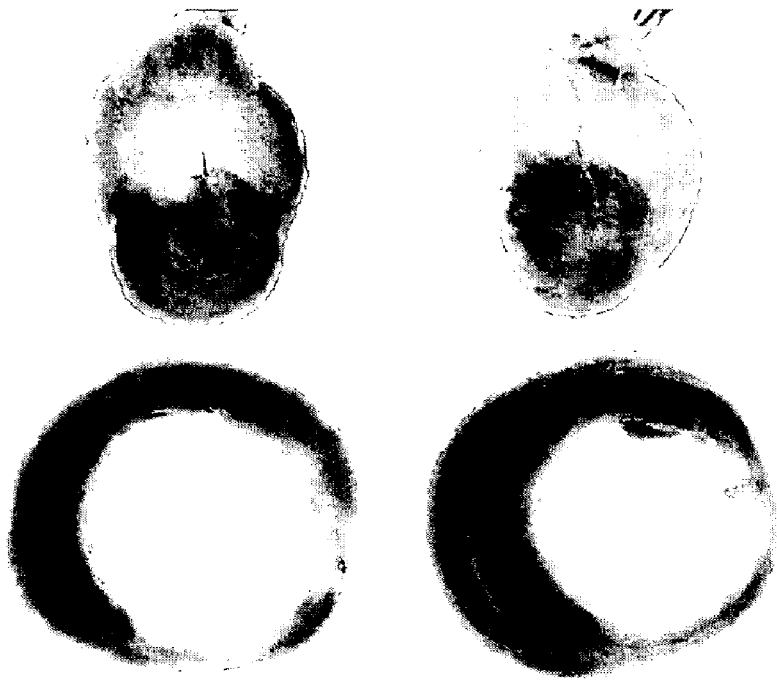
FIGS. 23A and 23B depict trangsenic Mst1 and nontransgenic animals 4 weeks after left coronary artery ligation to generate a myocardial infarction (MI) in vivo. (A) indicates that a similar size of myocardial infarction was created by ligation of the left coronary artery in non-transgenic (NTG) and transgenic (Tg-DN-Mst1) mice. LVEDD (B) and LVEF (B) were measured in sham operated and MI mice.
Figure 23B:
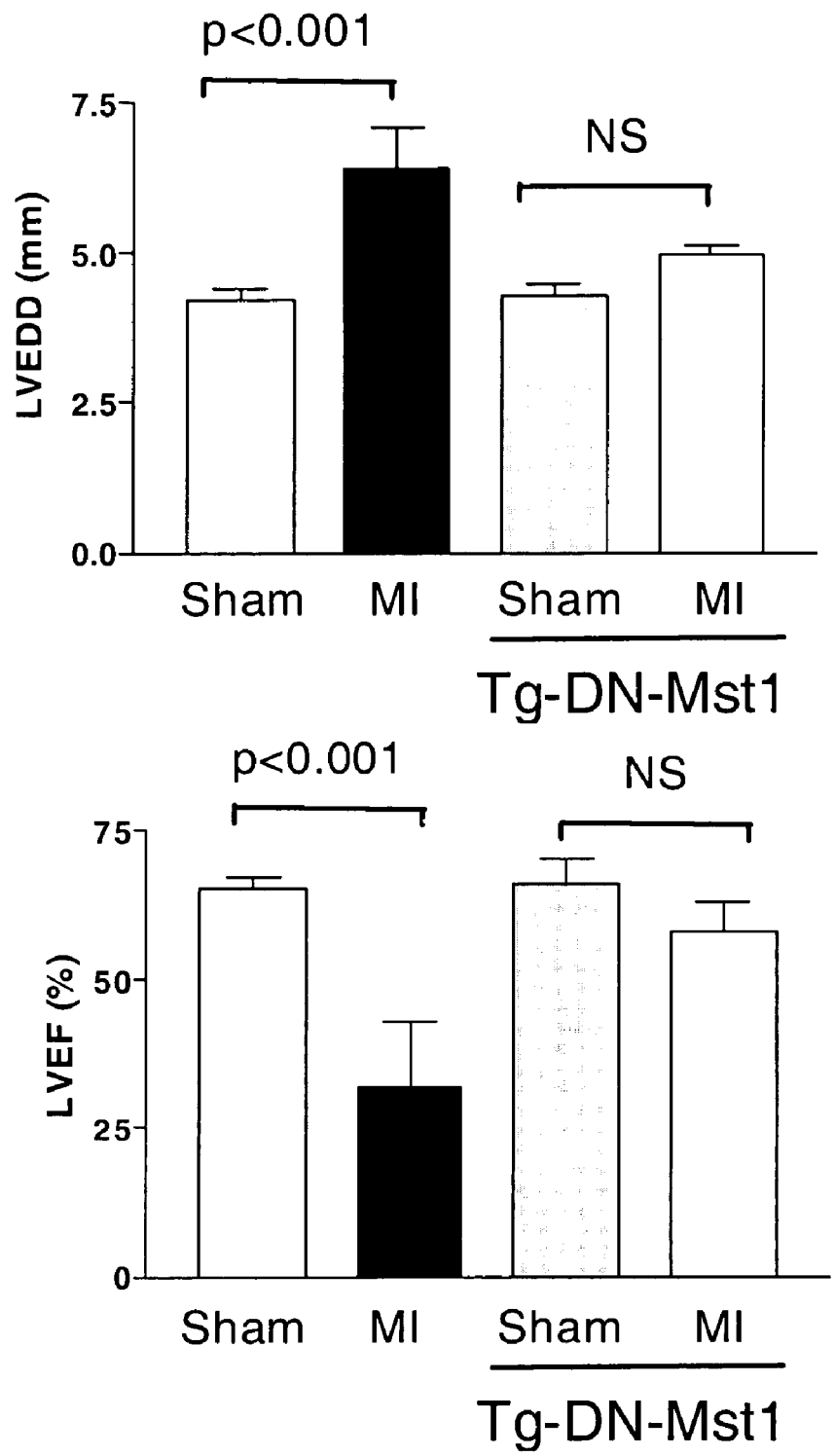

Overexpression of dominant negative Mst1 (Tg-DN-Mst1) inhibits cardiac dilation and left ventricular dysfunction after myocardial infarction. Myocardial infarction was generated by ligation of the left coronary artery in vivo in normal and Tg-DN-Mst1 transgenic mice. The results are depicted in FIG. 23. FIG. 23A (left panel) indicates that a similar size of myocardial infarction was created by ligation of the left coronary artery in non-transgenic (NTG) and transgenic (Tg-DN-Mst1) mice. LVEDD (FIG. 23B) and LVEF (FIG. 23C) were measured in sham operated and MI mice. The results suggest that dominant negative Mst1 may prevent cardiac dysfunction in post-MI patients.

Materials and Methods

Materials

Chelerythrine chloride, calyculin A and a caspase-3 inhibitor DEVD-CHO were purchased from Biomol (Plymouth Meeting, Pa.).

Primary Culture of Neonatal Rat Ventricular Myocytes

Primary cultures of ventricular cardiac myocytes were prepared from 1-day-old Crl: (WI) BR-Wistar rats (Charles River Laboratories, Wilmington, Mass.) as described previously (34). A cardiac myocyte rich fraction was obtained by centrifugation through the discontinuous Percoll gradient as described (34). Cells were cultured in the cardiac myocyte culture medium containing Dulbecco's modified Eagle medium (DMEM)/F12 supplemented with 5% horse serum, 4 µg/mL transferrin, 0.7 ng/mL sodium selenite (GIBCO), 2 g/L bovine serum albumin (fraction V), 3 mmol/L pyruvic acid, 15 mmol/L HEPES, 100 µmol/L ascorbic acid, 100 µg/mL ampicillin, 5 µg/mL linoleic acid and 100 µmol/L 5-bromo-2'-deoxyuridine (Sigma). We obtained myocyte cultures in which more than 95% were myocytes, as assessed by immunofluorescence staining with a monoclonal antibody against sarcomeric myosin (MF20). Culture media were changed to serum-free at 24–36 h and then subjected to adenovirus transduction. Myocytes were cultured in the serum-free condition for 48 h before experiments.

Construction of the Adenoviral Vectors

We constructed recombinant adenovirus by using an Adeno-X adenovirus construction kit according to the manufacturer's instruction (Clontech, Palo Alto, Calif.). We made replication defective human adenovirus type 5 (devoid of E1 and E3) harboring wild type Mst1 (AdX-Mst1) and dominant negative Mst1 (AdX-Mst1(K59R)). Adenovirus harboring α-galactosidase (Ad5 βgal) was used as a control. Generation of adenovirus harboring XIAP (Ad5 XIAP) has been described (35). The method of adenovirus transduction has been described (35).

Analysis of DNA Fragmentation by ELISA and DNA Laddering Assays

Histone-associated DNA fragments were quantified by the Cell Death Detection ELISA (Roche, Indianapolis, Ind.) according to the manufacturer's instruction as described (35) with minor modification for sample preparation. In brief, myocytes were rinsed with PBS three times in order to remove nucleosomes leaked out from necrotic cells and then incubated with the lysis buffer for 30 min. The supernatant containing mono- and oligonucleosomes from the cytoplasmic fraction of apoptotic cells was used for further analyses. DNA fragmentation of the tissue samples was determined by DNA laddering assays. Genomic DNA containing small molecular weight fragments was isolated and analyzed by agarose gel electrophoresis as described (36).

Immunoblot Analysis

For analyses of Mst1, cells were lysed in a Lysis Buffer A, containing 25 mmol/L NaCl, 25 mmol/L Tris (pH 7.4), 1 mmol/L $Na_3VO_4$, 10 mmol/L NaF, 10 mmol sodium pyrophosphate, 0.5 mmol/L EGTA, 0.5 mmol/L AEBSF, 0.5 µ/mL leupeptin, 0.5 µ/mL aprotinin. Samples containing the equal amount of protein were subjected to SDS-PAGE. Proteins were transferred onto polyvinylidene fluoride microporous membranes (Bio Rad, Hercules, Calif.) and probed with primary antibodies. We used anti-Mst1 monoclonal antibody (Transduction Laboratory, Lexington, Ky.) for detection of the carboxyl terminus of Mst1. Affinity purified rabbit polyclonal antibody was raised against animo-terminal ETVQLRNPPRRQLKC (pAb-15) (SEQ ID NO:4) (BioSource International, Camarillo, Calif.) for detection of the amino-terminus of Mst1. Blots were then probed by horseradish peroxidase-conjugated anti-mouse IgG or anti-rabbit IgG (Cell Signaling Technolog Inc., Beverly, Mass.). Antigen-antibody complexes were visualized by the enhanced chemiluminescence system (ECL, Amersham/Pharmacia, Piscataway, N.J.). Polyclonal antibodies raised against cleaved caspase-3 (Cell Signaling Technology Inc.) were used to determine activation of caspase-3, as described (35).

In Gel Kinase Assay

In gel myelin basic protein (MBP) kinase assays were performed as described previously (38). Either 100 □g of total cell lysates, heart homogenates, or immunoprecipitates of Mst1 were used. Immunoprecipitation of Mst1 was performed by incubating cell extracts (300 □g) with pAb-15 at 4° C. for 3 h followed by 40 □l slurry (50% v/v) of protein A at 4° C. for 1 h. The samples were washed with the lysis buffer (700 □L) for three times. The immunoprecipitates were boiled with the Laemmli's SDS-PAGE sample buffer before loading to SDS-PAGE gel.

Transgenic Mice

Mst1 and dominant negative Mst1 (DN-Mst1) transgenic mice (hereafter designated as Tg-Mst1 and Tg-DN-Mst1, respectively) were generated (C57BL/6 background) using a cDNA of human myc-Mst1 and myc-Mst1 (K59R) driven by the □-myosin heavy chain promoter (courtesy, Dr. J Robbins, University of Cincinnati) to achieve cardiac specific expression.

Echocardiography

Mice were anesthetized with an intraperitoneal injection of ketamine (0.065 mg/g), acepromazine (0.02 mg/g) and xylazine (0.013 mg/g). Echocardiography was performed using ultrasonography (Apogee CX-200; Interspec Inc., Ambler, Pa.) as described previously (39). A dynamically focused 9-MHz annular array transducer was applied from below, using a warmed saline bag as a standoff. M-mode measurements of LV internal diameter were made from more than 3 beats and averaged. Measurements of end-diastolic diameter (LVEDD) were taken at the time of the apparent maximal LV diastolic dimension, while measurements of the LV end-systolic diameter (LVESD) were taken at the time of the most anterior systolic excursion of the posterior wall. LV ejection fraction (LVEF) was calculated by the cubed method as follows: $LVEF=[(LVEDD)^3-(LVESD)^3]/(LVEDD)^3$.

Histological Analyses

The heart specimens were fixed with formalin, embedded in paraffin, and sectioned at 6 µm thickness. Interstitial fobrosis was evaluated by picric acid sirius red staining as described (40). Myocyte cross-sectional area was measured from images captured from silver-stained 1-µm-thick methacrylate sections as described (36,39,40). Suitable cross-sections were defined as having nearly circular capillary profiles and circular-to-oval myocyte sections. No correction for oblique sectioning was made. The outline of 100–200 myocytes was traced in each section. The Meta-Morph image system software was used to determine myocyte cross-sectional area (36,39,40). The number of myocyte (N) in the sampled area (A) was measured according to the criteria described by Gundersen (48) using Image-Pro Plus software and the myocyte density was calculated as N/A. Using the histologically determined thickness of the LV free wall and the myocyte density per unit area of myocardium, the average number of myocytes across the ventricular wall was computed as described (49).

Evaluation of Apoptosis in Tissue Sections

DNA fragmentation was detected in situ by using terminal deoxyribonucleotide transferase (TdT)-mediated dUTP nick end-labeling (TUNEL) as described (36,39). Briefly, deparaffinized sections were incubated with proteinase K and DNA fragments were labeled with fluorescein-conjugated dUTP using TdT (Roche). Nuclear density was determined by manual counting of DAPI stained nuclei in 6 fields of each animal using the 40× objective, and the number of TUNEL positive nuclei counted by examining the entire section using the same power objective. Limiting the counting of total nuclei and the TUNEL-positive nuclei to areas with true cross section of myocytes made it possible to selectively count only those nuclei that clearly were within myocytes (36). For some samples, triple staining with DAPI, TUNEL, and MF20, and subsequent analyses using confocal microscopy were performed.

cDNA Expression Array Analyses

DNA microarray analyses were performed by using Atlas cDNA expression arrays (Clontech Mouse 1.2 Array-II) according to the manufacturer's instruction. For each analysis, mRNA was prepared from two hearts of either Tg-Mst1 or non-transgenic mice. Analyses of the expression pattern were conducted by using AtlasNavigator™ 2.0 (Clontech). Analyses were repeated three times, using three different sets of mRNA samples.

Isolation of Adult Mouse Cardiac Myocytes

Cardiac myocytes were isolated as described previously (41). Longitudinal length of ventricular cardiac myocytes was determined as described (41). Whole cell currents were recorded using patch-clamp techniques (50). Cell capacitance was measured using voltage ramps of 0.8V/s from a holding potential of −50 mV.

Measurement of Contractile and Relaxation Function

Cardiac myocytes were isolated as described previously (41). In brief, the heart was rapidly excised and submerged in $Ca^{2+}$-free Tyrode's solution containing: 140 mmol/L NaCl, 5.4 mmol/L KCl, 1 mmol/L $MgCl_2$, 0.33 mmol/L $Na_2H_2PO_4$, 10 mmol/L glucose, 5 mmol/L HEPES (pH7.4). The heart was digested using 75 U/mL each of collagenase 1 and 2 (Worthington) at 32±2° C. All solutions were continuously bubbled with 95% $O_2$ and 5% $CO_2$ during digestion.

Myocyte contraction was induced once per second (1 Hz) and its function was measured using a video motion edge detector (VED 103, Cresent Electronics) as described previously (41). The contractile property was determined by % contraction, while the relaxation property by TL70% (the time for 70% relaxation).

I/R Surgery In Vivo

Mice were anesthetized by intraperitoneal injection of pentobarbital sodium (60 mg/kg). A rodent ventilator (model 683, Harvard Apparatus, Holliston, Mass.) was used with 65% oxygen during the surgical procedure. Ventilation was provided by passing a 20-gauge catheter into the trachea. The animals were kept warm by using heat lamps and heating pads. Rectal temperature was monitored and maintained between 36.8 and 37.2° C. The chest was opened by a horizontal incision through the muscle between the ribs (3rd intercostal space). Ischemia was achieved by ligating the anterior descending branch of the left coronary artery (LAD) by using a 8-0 nylon suture, with a silicon tubing (1 mm OD) placed on top of the LAD, 2 mm below the border between left atrium and left ventricle. Regional ischemia was confirmed by ECG change (ST elevation). After occlusion for 20 min, the silicon tubing was removed to achieve reperfusion. The chest wall was closed by a 8-0 silk. The animal was removed from the ventilator and kept warm in the cage maintained at 37° C. overnight. Hearts were harvested after 24 hours of reperfusion.

Assessment of Area at Risk and Infarct Size

After I/R, the animals were re-anesthetized, intubated and chest was opened. After arresting the heart at the diastolic phase by KCl injection, the ascending aorta was canulated and perfused with saline to wash out blood. The LAD was occluded with the same suture, which had been left at the site of the ligation. To demarcate the ischemic area at risk (AAR), Alcian blue dye (1%) was perfused into the aorta and coronary arteries. Hearts were excised and LVs were sliced into 1-mm cross sections. The heart sections were then incubated with a 1% triphenyltetrazolium chloride (TTC) solution at 37° C. for 10 minutes. Viable myocardium stained red, and the infarct appeared pale. The infarct area (pale), the AAR (not blue), and the total LV area from both sides of each section were measured by using Adobe Photoshop software, and the values obtained were averaged. The weight of each section was measured by using a balance (Mettler, Columbus, Ohio). The percent area of infarction and AAR of each section were multiplied by the weight of the section and then totaled from all sections. AAR/LV and infarct area/AAR were calculated and expressed as a percentage. There was no significant difference in AAR/LV between Tg-DN-Mst1 and non-transgenic littermate control.

Statistics

All data are reported as mean±SEM. Statistical analyses between groups were done by one-way (ANOVA), and when F values were significant at a 95% confidence limit, differences among group means were evaluated using Fisher's project least significant difference post-test procedure for group data with a $p<0.05$ considered significant.

REFERENCES

1. Kajstura J, Cheng W, Reiss K, Clark W A, Sonnenblick E H, Krajewski R, Reed J D, Olivetti G, Anversa P, 1996. Apoptotic and necrotic myocyte cell death are independent contributing variables of infarct size in rats. *Lab. Invest.* 74:86–107.
2. Saraste A, Pulkki K, Kallajoki M, Henriksen K, Parvinen M, Voipio-Pulkki L M, 1997. Apoptosis in human acute myocardial infarction. *Circulation* 95:320–323.
3. Tanaka M, Ito H, Adachi S, Akimoto H, Nishikawa T, Kasajima T, Marumo F, Hiroe M, 1994. Hypoxia induces apoptosis with enhanced expression of fas antigen messenger RNA in cultured neonatal rat cardiomyocytes. *Circ. Res.* 75:426–433.
4. Bialik S, Geenen D L, Sasson I E, Cheng R, Homer J W, Evans S M, Lord E M, Koch C J, Kitsis R N, 1997. Myocyte apoptosis during acute myocardial infarction in the mouse localizes to hypoxic regions but occurs independently of p53. *J Clin Invest* 100: 1363–1372.
5. Gottlieb R A, Burleson K O, Kloner R A, Babior B M, Engler R L, 1994. Reperfusion injury induces apoptosis in rabbit cardiomyocytes. *J Clin Invest* 94:1621–1628.
6. Maulik N, Engelman R M, Rousou J A, Flack J E, 3rd, Deaton D, Das D K, 1999. Ischemic preconditioning reduces apoptosis by upregulating anti-death gene Bcl-2. *Circulation* 100:II369–375.
7. Webster K A, Discher D J, Kaiser S, Hernandez O, Sato B, Bishopric N H, 1999. Hypoxia-activated apoptosis of cardiac myocytes requires reoxygenation or a pH shift and is independent of p53. *J Clin Invest* 104:239–252.
8. Kang P M, Haunstetter A, Aoki H, Usheva A, Izumo S, 2000. Morphological and molecular characterization of adult cardiomyocyte apoptosis during hypoxia and reoxygenation. *Circ Res* 87:118–125.
9. Freude B, Masters T N, Robicsek F, Fokin A, Kostin S, Zimmermann R, Ullmann C, Lorenz-Meyer S, Schaper J, 2000. Apoptosis is initiated by myocardial ischemia and executed during reperfusion. *J Mol Cell Cardiol* 32:197–208.
10. Anversa P, 2000. Myocyte death in the pathological heart. *Circ Res* 86:121–124.
11. Elsasser A, Suzuki K, Lorenz-Meyer S, Bode C, Schaper J, 2001. The role of apoptosis in myocardial ischemia: a critical appraisal. *Basic Res Cardiol* 96:219–226.
12. Black S C, Huang J Q, Rezaiefar P, Radinovic S, Eberhart A, Nicholson D W, Rodger I W, 1998. Co-localization of the cysteine protease caspase-3 with apoptotic myocytes after in vivo myocardial ischemia and reperfusion in the rat. *J. Mol. Cell. Cardiol.* 30:733–742.
13. Bialik S, Cryns V L, Drincic A, Miyata S, Wollowick A L, Srinivasan A, Kitsis R N, 1999. The mitochondrial apoptotic pathway is activated by serum and glucose deprivation in cardiac myocytes. *Circ Res* 85:403–414.
14. Jeremias I, Kupatt C, Martin-Villalba A, Habazettl H, Schenkel J, Boekstegers P, Debatin K M, 2000. Involvement of CD95/Apo1/Fas in cell death after myocardial ischemia. *Circulation* 102:915–920.
15. de Moissac D, Gurevich R M, Zheng H, Singal P K, Kirshenbaum L A, 2000. Caspase activation and mitochondrial cytochrome C release during hypoxia-mediated apoptosis of adult ventricular myocytes. *J Mol Cell Cardiol* 32:53–63.
16. Chen M, He H, Zhan S, Krajewski S, Reed J C, Gottlieb R A, 2001. Bid is cleaved bycalpain to an active fragment in vitro and during myocardial ischemia/reperfusion. *J Biol Chem*:(in press).
17. Beltrami A P, Urbanek K, Kajstura J, Yan S M, Finato N, Bussani R, Nadal-Ginard B, Silvestri F, Leri A, Beltrami C A et al., 2001. Evidence that human cardiac myocytes divide after myocardial infarction. *N Engl J Med* 344: 1750–1757.
18. Ma X L, Kumar S, Gao F, Louden C S, Lopez B L, Christopher T A, Wang C, Lee J C, Feuerstein G Z, Yue T L, 1999. Inhibition of p38 mitogen-activated protein kinase decreases cardiomyocyte apoptosis and improves cardiac function after myocardial ischemia and reperfusion. *Circulation* 99:1685–1691.
19. Mackay K, Mochly-Rosen D, 1999. An inhibitor of p38 mitogen-activated protein kinase protects neonatal cardiac myocytes from ischemia. *J Biol Chem* 274:6272–6279.

20. Dougherty C J, Kubasiak L A, Prentice H, Andreka P, Bishopric N H, Webster K A, 2002. Activation of c-Jun N-terminal kinase promotes survival of cardiac myocytes after oxidative stress. *Biochem J* 362:561–571.

21. Aoki H, Kang P M, Hampe J, Yoshimura K, Noma T, Matsuzaki M, Izumo S, 2002. Direct activation of mitochondrial apoptosis machinery by c-Jun N-terminal kinase in adult cardiac myocytes. *J Biol Chem* 277: 10244–10250.

22. Bishopric N H, Andreka P, Slepak T, Webster K A, 2001. Molecular mechanisms of apoptosis in the cardiac myocyte. *Curr Opin Pharmacol* 1:141–150.

23. Hreniuk D, Garay M, Gaarde W, Monia B P, McKay R A, Cioffi C L, 2001. Inhibition of c-Jun N-terminal kinase 1, but not c-Jun N-terminal kinase 2, suppresses apoptosis induced by ischemia/reoxygenation in rat cardiac myocytes. *Mol Pharmacol* 59:867–874.

24. Creasy C L, Chernoff J, 1995. Cloning and characterization of a human protein kinase with homology to Ste20. *J Biol Chem* 270:21695–21700.

25. Taylor L K, Wang H C, Erikson R L, 1996. Newly identified stress-responsive protein kinases, Krs-1 and Krs-2. *J. Biol. Chem.* 271:32487–32490.

26. Kyriakis J M, 1999. Signaling by the germinal center kinase family of protein kinases. *J Biol Chem* 274: 5259–5262.

27. Dan I, Watanabe N M, Kusumi A, 2001. The Ste20 group kinases as regulators of MAP kinase cascades. *Trends Cell Biol* 11:220–230.

28. Lee K K, Murakawa M, Nishida E, Tsubuki S, Kawashima S, Sakamaki K, Yonehara S, 1998. Proteolytic activation of MST/Krs, STE20-related protein kinase, by caspase during apoptosis. *Oncogene* 16:3029–3037.

29. Kakeya H, Onose R, Osada H, 1999. Activation of a 36-kD MBP kinase, an active proteolytic fragment of MST/Krs proteins, during anticancer drug-induced apoptosis. *Ann NY Acad Sci* 886:273–275.

30. Graves J D, Gotoh Y, Draves K E, Ambrose D, Han D K M, Wright M, Chernoff J, Clark E A, Krebs E G, 1998. Caspase-mediated activation and induction of apoptosis by the mammalian Ste-20 like kinase Mst1. *EMBO J.* 8:2224–2234.

31. Lee K K, Ohyama T, Yajima N, Tsubuki S, Yonehara S, 2001. Mst, a physiological caspase substrate, highly sensitizes apoptosis both upstream and downstream of caspase activation. *J Biol Chem* 276:19276–19285.

32. Ura S, Masuyama N, Graves J D, Gotoh Y, 2001. MST1-JNK promotes apoptosis via caspase-dependent and independent pathways. *Genes Cells* 6:519–530.

33. Yamamoto S, Seta K, Sadoshima J, 2000. Mst1 (Mammalian Ste20-like Kinase) is a Prominent Renaturable MBP Kinase Cleaved by Caspase and Enhanced Appoptosis in Cardiac Myocytes. *Circulation* 102.

34. Aoki H, Izumo S, Sadoshima J, 1998. Angiotensin II activates RhoA in cardiac myocytes: a critical role of RhoA in angiotensin II-induced premyofibril formation. *Circ. Res.* 81:666–676.

35. Yamamoto S, Seta K, Morisco C, Vatner S, Sadoshima J, 2001. Chelerythrine rapidly induces apoptosis through generation of reactive oxygen species in cardiac myocytes. *J. Mol. Cell. Cardiol.* 33:1829–1848.

36. Geng Y J, Ishikawa Y, Vatner D E, Wagner T E, Bishop S P, Vatner S F, Homcy C J, 1999. Apoptosis of cardiac myocytes in Gsalpha transgenic mice. *Circ Res* 84:34–42.

37. Sadoshima J, Izumo S, 1997. The cellular and molecular response of cardiac myocytes to mechanical stress. *Annu. Rev. Physiol.* 59:551–571.

38. Sadoshima J, Qiu Z, Morgan J P, Izumo S, 1995. Angiotensin II and other hypertrophic stimuli mediated by G protein-coupled receptors activate tyrosine kinase, mitogen-activated protein kinase, and 90-kD S6 kinase in cardiac myocytes: the critical role of $Ca^{2+}$-dependent signaling. *Circ. Res.* 76:1–15.

39. Asai K, Yang G P, Geng Y J, Takagi G, Bishop S, Ishikawa Y, Shannon R P, Wagner T E, Vatner D E, Homcy C J et al., 1999. Beta-adrenergic receptor blockade arrests myocyte damage and preserves cardiac function in the transgenic G(salpha) mouse. *J Clin Invest* 104:551–558.

40. Yang G, Meguro T, Hong C, Asai K, Takagi G, Karoor V L, Sadoshima J, Vatner D E, Bishop S P, F. V S, 2001. Cyclosporine reduces left ventricular mass with chronic aortic banding in mice, which could be due to apoptosis and fibrosis. *J. Mol. Cell. Cardiol.* 33:1505–1514.

41. Kim S J, Yatani A, Vatner D E, Yamamoto S, Ishikawa Y, Wagner T E, Shannon R P, Kim Y K, Takagi G, Asai K et al., 1999. Differential regulation of inotropy and lusitropy in overexpressed Gsalpha myocytes through cAMP and Ca2+ channel pathways. *J Clin Invest* 103: 1089–1097.

42. Lee K K, Yonehara S, 2002. Phosphorylation and dimerization regulate nucleocytoplasmic shuttling of mammalian STE20-like kinase (MST). *J Biol Chem* 277: 12351–12358.

43. Brewis N, Ohst K, Fields K, Rapacciuolo A, Chou D, Bloor C, Dillmann W, Rockman H, Walter G, 2000. Dilated cardiomyopathy in transgenic mice expressing a mutant A subunit of protein phosphatase 2A. *Am J Physiol Heart Circ Physiol* 279:H1307–1318.

44. Ide T, Tsutsui H, Hayashidani S, Kang D, Suematsu N, Nakamura K, Utsumi H, Hamasaki N, Takeshita A, 2001. Mitochondrial DNA damage and dysfunction associated with oxidative stress in failing hearts after myocardial infarction. *Circ Res* 88:529–535.

45. Moncada S, Erusalimsky J D, 2002. Does nitric oxide modulate mitochondrial energy generation and apoptosis? *Nat Rev Mol Cell Biol* 3:214–220.

46. Khokhlatchev A, Rabizadeh S, Xavier R, Nedwidek M, Chen T, Zhang X, Seed B, Avruch J, 2002. Identification of a novel ras-regulated proapoptotic pathway. *Curr Biol* 12:253–265.

47. Reed, J. C., and Paternostro, G. 1999. Postmitochondrial regulation of apoptosis during heart failure. *Proc Natl Acad Sci USA* 96:7614–7616.

48. Gundersen, H. J. G. 1977. Notes on the estimation of the numerical density of arbitrary profiles: The edge effect. *J. Microsc* 111:219–223.

49. Olivetti, G., Capasso, J. M., Sonnenblick, E. H., and Anversa, P. 1990. Side-to-side slippage of myocytes participates in ventricular wall remodeling acutely after myocardial infarction in rats. *Circ Res* 67:23–34.

50. Masaki, H., Sato, Y., Luo, W., Kranias, E. G., and Yatani, A. 1997. Phospholamban deficiency alters inactivation kinetics of L-type Ca2+ channels in mouse ventricular myocytes. *Am J Physiol* 272:H606–612.

51. Lin, Y., Khokhlatchev, A., Figeys, D., and Avruch, J. 2002. Death-associated Protein 4 Binds MST1 and Augments MST1-induced Apoptosis. *J Biol Chem* 277:47991–48001.

52. Khokhlatchev, A., Rabizadeh, S., Xavier, R., Nedwidek, M., Chen, T., Zhang, X., Seed, B., and Avruch, J. 2002. Identification of a novel ras-regulated proapoptotic pathway. *Curr Biol* 12:253–265.
53. Olivetti, G., Abbi, R., Quaini, F., Kajstura, J., Cheng, W., Nitahara, J. A., Quaini, E., Di Loreto, C., Beltrami, C. A., Krajewski, S., et al. 1997. Apoptosis in the failing human heart. *N Engl J Med* 336:1131–1141.

This invention may be embodied in other forms or carried out in other ways without departing from the spirit or essential characteristics thereof. The present disclosure is therefore to be considered as in all aspects illustrate and not restrictive, the scope of the invention being indicated by the appended claims, and all changes which come within the meaning and range of equivalency are intended to be embraced therein.

Various references are cited throughout this Specification, each of which is incorporated herein by reference in its entirety.

What is claimed is:

1. A method of treating cardiac disease in a mammal comprising administering to said mammal an effective amount of a compound or agent that blocks or otherwise specifically inhibits mammalian Ste20-like kinase (Mst1) wherein said compound is an Mst1 inhibitor which is a dominant negative mutant of Mst1.

2. The method of claim 1 wherein said dominant negative mutant of Mst1 is K59R.

3. The method of claim 1 wherein said cardiac disease is selected from the group of congestive heart failure, cardiomyopathy, including ischemic and nonischemic cardiomyopathy, coronary artery disease, arrhythmias, fibrosis of the heart, valve defects, atherosclerosis, and instances where facilitation of enhanced heart function or maintenance of cardiac myocytes is desired.

4. The method of claim 1 wherein said mammal is a human.

5. A method of modulating cardiac myocyte apoptosis in a mammal comprising administering to said mammal an effective amount of a compound or agent that blocks or otherwise specifically inhibits mammalian Ste20-like kinase (Mst1) wherein said compound is an Mst1 inhibitor which is a dominant negative mutant of Mst1.

6. The method of claim 5 wherein said dominant negative mutant of Mst1 is K59R.

7. A method for treating cardiac disease in a mammal comprising administering to said mammal an effective amount of a compound or agent that blocks or otherwise specifically inhibits mammalian Ste20-like kinase (Mst1) wherein said compound is an Mst1 inhibitor which is a dominant negative mutant of Mst1.

8. The method of claim 7 wherein said dominant negative mutant of Mst1 is K59R.

9. A method for treating cardiac disease in a mammal comprising administering to said mammal an effective amount of a compound or agent that blocks or otherwise specifically inhibits mammalian Ste20-like kinase (Mst1) wherein said compound is an Mst1 inhibitor which is a dominant negative mutant of Mst1, in combination with one or more other compounds for treatment of cardiac disease or of atherosclerosis.

10. The method of claim 9 wherein said dominant negative mutant of Mst1 is K59R.

11. The method of claim 9 wherein said one or more other compound is selected from the group of a beta-blocker, nitrate, calcium channel antagonists, angiotensin-converting enzyme (ACE) inhibitors, an anti-platelet drug, diuretics, digoxin and antilipemic agents, agents which alter cholesterol or lipid metabolism.

12. A method for reducing the risk of cardiomyopathy or cardiac dysfunction in a mammal wherein said mammal has suffered a myocardial infarct or other coronary event wherein blood flow to the heart is reduced comprising administering to said mammal an effective amount of a compound or agent that blocks or otherwise specifically inhibits mammalian Ste20-like kinase (Mst1) wherein said compound is an Mst1 inhibitor which is a dominant negative mutant of Mst1.

13. The method of claim 12 wherein said dominant negative mutant of Mst1 is K59R.

14. A method of cardioprotection in a mammal, wherein a specific inhibitor of Mst1 is a dominant negative mutant of mammalian Ste20-like kinase (Mst1) and is administered to said mammal in conjunction with or following therapy with a compound or drug which is cardiotoxic.

15. The method of claim 14 wherein said dominant negative mutant of Mst1 is K59R.

16. The method of claim 14 wherein said compound is a chemotherapeutic agent, particularly an anti-cancer or anti-tumor agent.

17. The method of claim 14 wherein said chemotherapeutic agent is doxorubicin.

* * * * *

SEQUENCE LISTING

```
<160> NUMBER OF SEQ ID NOS: 4

<210> SEQ ID NO 1

<400> SEQUENCE: 1

000

<210> SEQ ID NO 2
<211> LENGTH: 1464
<212> TYPE: DNA
<213> ORGANISM: Homo sapiens

<400> SEQUENCE: 2
atggagacgg tacagctgag gaacccgccg cgccggcagc tgaaaaagtt ggatgaagat      60
agtttaacca aacaaccaga agaagtattt gatgtcttag agaaacttgg agaagggtcc     120
tatggcagcg tatacaaagc tattcataaa gagaccggcc agattgttgc tattaagcaa     180
gttcctgtgg aatcagacct ccaggagata atcaaagaaa tctctataat gcagcaatgt     240
gacagccctc atgtagtcaa atattatggc agttatttta agaacacaga cttatggatc     300
gttatggagt actgtgggc tggttctgta tctgatatca ttcgattacg aaataaaacg       360
ttaacagaag atgaaatagc tacaatatta caatcaactc ttaagggact tgaataccett    420 cattttatga gaaaaataca ccgagatatc aaggcaggaa atattttgct aaatacagaa      480
ggacatgcaa aacttgcaga ttttggggta gcaggtcaac ttacagatac catggccaag     540
cggaatacag tgataggaac accattttgg atggctccag aagtgattca ggaaattgga     600
tacaactgtg tagcagacat ctggtccctg ggaataactg ccatagaaat ggctgaagga     660 aagcccctt atgctgatat ccatccaatg agggcaatct tcatgattcc tacaaatcct      720
cctcccacat tccgaaaacc agagctatgg tcagataact ttacagattt tgtgaaacag     780
tgtcttgtaa agagccctga gcagagggcc acagccactc agctcctgca gcacccattt     840
gtcaggagtg ccaaaggagt gtcaatactg cgagacttaa ttaatgaagc catggatgtg     900
aaactgaaac gccaggaatc ccagcagcgg gaagtggacc aggacgatga agaaaactca     960
gaagaggatg aaatggattc tggcacgatg gttcgagcag tgggtgatga gatgggcact    1020
gtccgagtag ccagcaccat gactgatgga gccaatacta tgattgagca cgatgacacg    1080
ttgccatcac aactgggcac catggtgatc aatgcagagg atgaggaaga ggaaggaact    1140
atgaaaagaa gggatgagac catgcagcct gcgaaaccat cctttcttga atattttgaa    1200
caaaaagaaa aggaaaacca gatcaacagc tttgcaaga gtgtacctgg tccactgaaa    1260
aattcttcag attggaaaat accacaggat ggagactacg agtttcttaa gagttggaca    1320
gtggaggacc ttcagaagag gctcttggcc ctggacccca tgatggagca ggagattgaa    1380
```

```
gagatccggc agaagtacca gtccaagcgg cagcccatcc tggatgccat agaggctaag    1440
aagagacggc aacaaaactt ctga                                           1464

<210> SEQ ID NO 3

<400> SEQUENCE: 3

000

<210> SEQ ID NO 4
<211> LENGTH: 15
<212> TYPE: PRT
<213> ORGANISM: Homo sapiens

<400> SEQUENCE: 4

Glu Thr Val Gln Leu Arg Asn Pro Pro Arg Arg Gln Leu Lys Cys
1               5                   10                  15
```